(12) United States Patent
Suau et al.

(10) Patent No.: US 7,790,800 B2
(45) Date of Patent: Sep. 7, 2010

(54) USE OF WATER-SOLUBLE ACRYLIC COPOLYMERS IN OPTIONALLY PIGMENTED AQUEOUS FORMULATIONS AND RESULTING FORMULATIONS

(75) Inventors: Jean-Marc Suau, Lucenay (FR); Yves Kensicher, Theize (FR); Denis Ruhlmann, Genay (FR)

(73) Assignee: Coatex S.A.S., Genay (FR)

( * ) Notice: Subject to any disclaimer, the term of this patent is extended or adjusted under 35 U.S.C. 154(b) by 632 days.

(21) Appl. No.: 11/631,474

(22) PCT Filed: Jul. 5, 2005

(86) PCT No.: PCT/FR2005/001714

§ 371 (c)(1),
(2), (4) Date: Jan. 31, 2007

(87) PCT Pub. No.: WO2006/016035

PCT Pub. Date: Feb. 16, 2006

(65) Prior Publication Data

US 2008/0103248 A1    May 1, 2008

(30) Foreign Application Priority Data

Jul. 8, 2004 (FR) .................................. 04 07570

(51) Int. Cl.
  *C08F 20/08* (2006.01)
  *C08F 120/04* (2006.01)
  *C08F 20/44* (2006.01)
  *C08F 26/10* (2006.01)
(52) U.S. Cl. ................. 524/548; 524/556; 524/565; 526/263; 526/264; 526/271; 526/317.1; 526/318.3
(58) Field of Classification Search ............... 524/548, 524/556, 565; 526/263, 264, 271, 317.1, 526/318.3
See application file for complete search history.

(56) References Cited

U.S. PATENT DOCUMENTS

| 5,294,693 | A | 3/1994 | Egraz et al. |
| 5,362,415 | A | 11/1994 | Egraz et al. |
| 5,423,999 | A | 6/1995 | Egraz et al. |
| 5,474,702 | A | 12/1995 | Egraz et al. |
| 6,946,510 | B2 | 9/2005 | Suau et al. |
| 7,153,496 | B2 * | 12/2006 | Tamareselvy et al. .... 424/70.11 |
| 7,420,014 | B2 * | 9/2008 | Morihiro et al. ............ 524/558 |
| 2003/0202953 | A1 * | 10/2003 | Tamareselvy et al. .... 424/70.16 |
| 2005/0143511 | A1 | 6/2005 | Suau et al. |

FOREIGN PATENT DOCUMENTS

| EP | 1 403 347 | 3/2004 |
| EP | 1403347 A1 * | 3/2004 |
| FR | 2 693 203 | 1/1994 |

* cited by examiner

Primary Examiner—David Wu
Assistant Examiner—Michael M Bernshteyn
(74) Attorney, Agent, or Firm—Oblon, Spivak, McClelland, Maier & Neustadt, L.L.P.

(57) ABSTRACT

The invention concerns the use as a thickening agent, in possibly pigmented aqueous formulations, such as coating formulations such as paints in the aqueous phase such as dispersion paints, varnishes, paper coatings, cosmetic formulations, detergent formulations, textile formulations and drilling muds, of a water-soluble acrylic copolymer consisting of at least one monomer with ethylenic unsaturation and a carboxylic function, at least one non-ionic monomer with ethylenic unsaturation, at least one oxyalkylated monomer with ethylenic unsaturation terminated by a hydrophobic branched and non-aromatic chain with 10 to 24 carbon atoms, and possibly at least one monomer with at least two ethylenic unsaturations.

The invention also concerns the possibly pigmented aqueous formulations obtained.

19 Claims, No Drawings

USE OF WATER-SOLUBLE ACRYLIC COPOLYMERS IN OPTIONALLY PIGMENTED AQUEOUS FORMULATIONS AND RESULTING FORMULATIONS

The present invention concerns the sector of possibly pigmented aqueous formulations.

The invention concerns firstly the use as a thickening agent, in possibly pigmented aqueous formulations, such as coating formulations such as paints in aqueous phase and notably dispersion paints, varnishes, paper coatings, cosmetics, detergence, textile formulations and drilling muds, of a water-soluble acrylic copolymer consisting of at least one monomer with ethylenic unsaturation and a carboxylic function, at least one non-ionic monomer with ethylenic unsaturation, at least one oxyalkylated monomer with ethylenic unsaturation terminated by a hydrophobic branched and non-aromatic chain with 10 to 24 carbon atoms, and possibly at least one monomer called a crosslinking monomer, having at least two ethylenic unsaturations.

The invention also concerns the thickening agent enabling an optimum development and/or optimum maintenance of the viscosity of the aqueous formulations to be obtained in the presence of compounds, whether or not water-soluble, or when the said compounds are added to the said aqueous formulations.

The invention also concerns the process of manufacture of the said possibly pigmented aqueous formulations.

Finally, the invention concerns the possibly pigmented aqueous formulations obtained according to the invention.

In the field of aqueous formulations possibly containing one or more mineral fillers, and more particularly in the sector of paints in the aqueous phase, and notably dispersion paints, controlling the rheology of the said formulations, both at the stage of manufacture and during their transport and storage, and during their use, is one of the fundamental goals for the skilled man in the art. The wide variety of practical constraints in each of these stages relates to a multiplicity of different rheological properties. Nevertheless, it is possible to summarise the requirement of the skilled man in the art in obtaining an effect of the thickening of the aqueous formulation, both for reasons of stability over time, and for a possible application of the paint to a vertical surface, lack of splashing during use, or of dripping after application, etc. As a consequence, the products which contribute to this regulation of the rheological properties have been designated under the term "thickening agents".

Historically, since the 1950s cellulose-based gums and thickening agents have been used, one of the essential characteristics of which is their high molecular weight. However, these compounds have a number of disadvantages, such as their instability over time, as is recalled by document U.S. Pat. No. 4,673,518, the need of using a large quantity of them, highlighted in document EP 0 250 943, and the production costs which they engender (notably in terms of waste treatment), as indicated in document U.S. Pat. No. 4,384,096.

The skilled man in the art then turned towards a new category of thickening agents, known as the "associative" thickening agents, the operational mechanism and the characteristics of which are now well-known, and recalled in document "Rheology modifiers for water-borne paints" (Surface Coatings Australia, October 1985, pp 6). These are water-soluble polymers with insoluble hydrophobic groupings, creating the associative effect through the interaction of these hydrophobic groupings with the surface of the binder particles in dispersion, thus producing a three-dimensional network which causes the viscosity of the medium to increase.

It is possible to distinguish very schematically among the synthetic polymers the polyurethane associative thickening agents from the acrylic associative thickening agents.

Such thickening agents are now commonly used, among other sectors, in the sector of paints in aqueous phase, and notably dispersion paints. However, their use is not devoid of disadvantages, including two major ones, which the Applicant wishes to develop here. The first concerns the "sensitivity to compounds, whether or not water-soluble" (and notably salts and surfactants), and the second the "pigmentary compatibility" or "colour acceptance". These problems are encountered in a large number of aqueous formulations, such as paints in aqueous phase, and notably dispersion paints, but also formulations such as cosmetic or detergent formulations. Each of these problems will subsequently be envisaged from the standpoint of the solutions proposed by the state of the technique, from the viewpoints of both the associative acrylic thickening agents, and the associative polyurethane thickening agents.

"Sensitivity to compounds, whether or not water-soluble" designates the properties of a thickening agent which, when it is put in presence of such compounds, and notably salts and surfactants, tends no longer to maintain the viscosity at a satisfactory degree for the skilled man in the art or the user of these aqueous formulations. The resulting loss of viscosity is prejudicial for the storage and application qualities of the said formulations. This type of phenomenon is widely reported in the literature, particularly in respect of the associative acrylic thickening agents, as is emphasised by document EP 0 013 836, which relates the sensitivity to salts, and notably sodium chloride, of such additives. This document teaches the skilled man in the art the manufacture of associative acrylic thickening agents from a monomer chosen from among acrylic acid and methacrylic acid, from a monomer which is an alkyl ester, and from a hydrophobic monomer with a radical having 8 to 30 carbon atoms. Its principal function is to improve the rheological profile of the aqueous paints in which it is used. Similarly, document EP 0 011 806 teaches the manufacture of other associative acrylic thickening agents, from a carboxylic monomer, from ethyl acrylate, and from a hydrophobic monomer with an alkyl radical or phenyl alkyl having 8 to 20 carbon atoms. Finally, document EP 0 577 526 describes associative acrylic thickening agents having a base of a carboxylic monomer, a monomer with ethylenic but not carboxylated unsaturation, and an oxyalkylated monomer terminated by a hydrophobic fatty chain. Nevertheless, in terms of insensitivity to the salts, these copolymers do not give the skilled man in the art satisfaction.

Another problem with which the skilled man in the art is faced is that of pigmentary compatibility. In terms of paint formulation, the term "base" or "white base" designates the pigmented aqueous composition charged with white colour, which acts as the base of the coloured pigmentary or final pigmented composition.

This aqueous composition charged and/or pigmented with white colour is formed from a liquid phase which may be water, or an organic solvent which is miscible in water or, again, a blend of both, from one or more polymers in solution or in suspension in the liquid phase called "binders", from fillers and/or pigments, from at least one filler and/or pigment dispersing agent, which may be a water-soluble polymer or copolymer, from additives as diverse as coalescence agents, biocides, anti-foaming agents, or others, and finally from at least one thickening agent which is a natural or synthetic polymer or copolymer. When the coloured pigments are added to the said "bases" of white colour, in the form of pigmentary concentrates or pigmentary pastes, the resulting pigmentary formulation is obtained.

The composition of the coloured pigment concentrates or pigmentary concentrates or pigmentary pastes generally also contains additives or compounds of the surfactant type or electrolyte salt type, or a co-solvent miscible in water in large quantities.

The pigmentary concentrates most commonly used are said to be universal, since they can be added not only to paints in the aqueous phase, but also to paints in solvent phase.

In practice, if the final formulation has insufficient pigmentary compatibility, firstly there may be an effect on the rheology of the resulting pigmentary formulation, and secondly there may be an effect on the colouring force developed by the pigment or pigments of the pigmentary concentrate or concentrates in the resulting pigmentary formulation.

This loss of colouring force may lead to a paint film the hue of which is uniformly more "washed out", soiled or degraded towards white compared to the reference. Clearly, this loss of colouring force is very prejudicial to the tinting of paint by an automated system according to the measurement of a spectrophotocolorimeter, as this is practised in large DIY stores or in paint retailers.

Indeed, the computer will compute that a certain quantity of universal pigmentary concentrates should enable the desired hue to be approached, but the loss of colouring force relating to this poor compatibility will distort the result.

This phenomenon may be measured by the use of a spectrophotocolorimeter enabling the three-chromatic coordinates to be measured (Huntsmann: L*,a*,b*) and thus the colour of a dry paint film.

L* will give a value in the scale of greys (the higher and more positive L* the lighter the film; the smaller and the more negative L* the darker the film). The second coordinate, a*, characterises the colour in a scale ranging from green to red (the higher and more positive a* the more red the film; the smaller and more negative a* the more green the film). The third coordinate, b*, characterises the colour in a scale ranging from blue to yellow (the higher and more positive b* the more yellow the film; the smaller and more negative b* the more blue the film).

In certain rarer cases one even observes variations of hues in different zones in a given paint film. These variations are related to the shear differences to which these different zones are subjected when the paint film is applied with a tools such as, for example, a paintbrush. Universal colouring pigments which are poorly dispersed in the paint will express a colouring force which will depend on the shear stress to which the paint containing them is subjected. In the case of the use of a paintbrush, this phenomenon will emphasise the brushstrokes (where the hairs of the brush are more strongly applied), giving them a colour different from the rest of the paint film. To visualise this phenomenon, the skilled man in the art may apply to the paintbrush or use a test known as a rub-out test, consisting in applying a paint film uniformly, without any shear difference, using a block, and then in shearing a part of the paint film which is still fresh, non-dry, with a finger. The sheared zone may become lighter or darker than the non-sheared zone.

Along the same lines, the skilled man in the art is familiar with document U.S. Pat. No. 5,973,063, which describes a polyurethane associative thickening agent, and also with document FR 2 826 014, which teaches that it is possible, by selecting a polyisocyanate-based compound having at the end of the chain hydrocarbonated groupings with at least three aromatic cycles, to manufacture a polyurethane thickening agent having a satisfactory pigmentary compatibility, and developing a high viscosity under a low shear value.

Consequently, the skilled man in the art, who is seeking to make available to the end user an aqueous composition the Theological profile of which remains acceptable in the presence of compounds, whether or not water-soluble, or when the said compounds are added, such as the salts or surfactants in the field of detergence or cosmetics, or again such as the universal pigmentary concentrates in the field of paint, notably under a low shear value, to obtain satisfactory spreading of the paint, is faced with the problems of the greatly reduced viscosity of the formulation in the presence of the said compounds, and naturally turns towards the associative thickening agents of the polyurethane type. The latter, as we have just seen, are well known to offer a high resistance to salts, and to develop an appropriate viscosity under a low shear.

The final document FR 2 826 014 finally demonstrated that the "polyurethane approach" also authorises the manufacture of such thickening agents having a satisfactory pigmentary compatibility.

And, continuing their research with a view to improving the stability of the viscosity of the aqueous formulations in the presence of compounds, whether water-soluble or non-water-soluble, or when the said compounds are added to the said aqueous formulations, and of improving the pigmentary compatibility, whilst maintaining a viscosity of the formulation acceptable for the end user, the Applicant found in a completely surprising manner that all these problems may be resolved by the selection of the oxyalkylated monomer with ethylenic unsaturation of the copolymer which is an associative acrylic thickening agent, and by its use as an additive in the formulation.

This water-soluble acrylic copolymer consists of a least one monomer with ethylenic unsaturation and with a carboxylic function, at least one non-ionic monomer with ethylenic unsaturation, at least one oxyalkylated monomer with ethylenic unsaturation terminated by a hydrophobic branched, non-aromatic chain with 10 to 24 carbon atoms, and possibly at least one monomer called a crosslinking monomer, with at least two ethylenic unsaturations.

The object of the invention is thus the use in possibly pigmented aqueous formulations, such as coating formulations such as paints in the aqueous phase and notably dispersion paints, varnishes, paper coatings, cosmetics, detergence, textile formulations and drilling muds, of this copolymer as a thickening agent enabling a development and/or maintenance of the viscosity of the aqueous formulations to be obtained in the presence of compounds, whether or not water-soluble, or when the said compounds are added to the said aqueous formulations.

Another object of the invention is the thickening agent constituted by this water-soluble acrylic copolymer consisting of a least one monomer with ethylenic unsaturation and with a carboxylic function, at least one non-ionic monomer with ethylenic unsaturation, at least one oxyalkylated monomer with ethylenic unsaturation terminated by a hydrophobic branched, non-aromatic chain with 10 to 24 carbon atoms, and possibly at least one monomer called a crosslinking monomer, with at least two ethylenic unsaturations.

Another object of the invention is the process of manufacture of the possibly pigmented aqueous formulations.

A final object of the invention lies in the possibly pigmented aqueous formulations obtained according to the invention.

These possibly pigmented aqueous formulations containing the thickening agent according to the invention are coating aqueous formulations chosen from among dispersion paints, varnishes, paper coatings, cosmetic formulations, detergent formulations, textile formulations (preparation, printing or colouring), and drilling muds.

These formulations are also formulations for plasterboard such as joint filler for plasterboard, formulations for ceramics, formulations for leather, plaster formulations or again formulations for hydraulic binders such as mortar formulations.

According to the invention, the copolymers added to the aqueous formulations as thickening agents enable the possibly pigmented aqueous formulations to be given satisfactory rheological properties with a view to their application, and notably an increase of their viscosity under an average shear value.

The Applicant indicates that the expression "average shear value" is taken to mean in the present application any shear value, also called a velocity gradient, of between $20\ s^{-1}$ and $1000\ s^{-1}$.

In addition, these copolymers develop an excellent tolerance in relation to salts and surfactants which these formulations may contain. Finally, such copolymers give the aqueous formulations in which they are used a very satisfactory pigmentary compatibility.

These aims are attained thanks to the use, as a thickening agent enabling a development and/or maintenance of the viscosity of the aqueous formulations to be obtained in the presence of compounds, whether or not water-soluble, or when the said compounds are added to the said aqueous formulations, of water-soluble acrylic copolymers characterised in that the said copolymer consists:

a) of at least one monomer with ethylenic unsaturation and a carboxylic function, b) of at least one non-ionic monomer with ethylenic unsaturation, c) of at least one oxyalkylated monomer with ethylenic unsaturation terminated by a hydrophobic, non-aromatic branched chain with 10 to 24 carbon atoms, d) and possibly of at least one monomer called a crosslinking monomer, having at least two ethylenic unsaturations.

This copolymer is also characterised in that:

a) the monomer or monomers with ethylenic unsaturation and a carboxylic function are chosen from among the monomers with ethylenic unsaturation and with a monocarboxylic function such as acrylic or methacrylic acid, or again the diacid hemiesters such as the monoesters in $C_1$ to $C_4$ of maleic or itaconic acids, or their blends, or chosen from among the monomers with ethylenic unsaturation and a dicarboxylic function, such as crotonic, isocrotonic, cinnamic, itaconic, maleic acid, or again the anhydrides of carboxylic acids, such as maleic anhydride, b) the non-ionic monomer or monomers with ethylenic unsaturation are chosen from among the esters, amides or nitriles of acrylic and methacrylic acids, such as the acrylates or methacrylates or methyl, ethyl, butyl, 2-ethyl-hexyl, or from among acrylonitrile, vinyl acetate, styrene, methylstyrene, diisobutylene, vinylpyrrolidone, vinylcaprolactame, c) the oxyalkylated monomer or monomers with ethylenic unsaturation and terminated by a hydrophobic and non-aromatic branched chain with 10 to 24 carbon atoms, have the following formula:

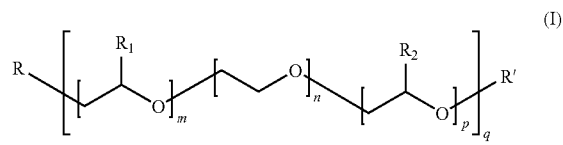

where:
m and p represent a number of alkylene oxide units of between 0 and 150, n represents a number of ethylene oxide units of between 5 and 150, q represents a whole number at least equal to 1 and such that $5 \leq (m+n+p)q \leq 150$, and preferentially such that $15 \leq (m+n+p)q \leq 120$, $R_1$ represents the methyl or ethyl radical, $R_2$ represents the methyl or ethyl radical, R represents a radical containing a polymerisable unsaturated function belonging to the group of acrylic, methacrylic, maleic, itaconic or crotonic esters, R' represents a hydrophobic and non-aromatic branched chain with 10 to 24 carbon atoms, d) the possible monomer or monomers, called crosslinking monomers, with at least two ethylenic unsaturations, are notably chosen from the group constituted by ethylene glycol diacrylate, ethylene glycol dimethacrylate, trimethylolpropanetriacrylate, trimethylolpropanetrimethacrylate, allyl acrylate, methylenebisacrylamide, methylenebismethacrylamide, tetrallyloxyethane, the triallylcyanurates, the allylic ethers obtained from polyols chosen from among pentaerythritol, sorbitol, or again sucrose.

In a preferential manner, the said copolymer is characterised in that the hydrophobic and non-aromatic branched chain has 12 to 24 carbon atoms, and has 2 branchings having at least 6 carbon atoms.

In a more preferential manner, the said copolymer is characterised in that the hydrophobic and non-aromatic branched chain has 16 to 20 carbon atoms, and has 2 branchings having at least 6 carbon atoms.

In an even more preferential manner, the hydrophobic non-aromatic branched chain is chosen from among 2-hexyl 1-decanyl and 2-octyl 1-dodecanyl.

This copolymer used as a thickening agent according to the invention is also characterised in that it contains, expressed by weight of monomers:

a) 2 to 95%, and preferentially 5 to 90% of at least one monomer with ethylenic unsaturation and a carboxylic function chosen from among the monomers with ethylenic unsaturation and with a monocarboxylic function such as acrylic or methacrylic acid, or again the diacid hemiesters such as the monoesters in $C_1$ to $C_4$ of maleic or itaconic acids, or their blends, or chosen from among the monomers with ethylenic unsaturation and a dicarboxylic fluction, such as crotonic, isocrotonic, cinnamic, itaconic, maleic acid, or again the anhydrides of carboxylic acids, such as maleic anhydride, b) 2 to 95%, and preferentially 5 to 90%, of at least one monomer with ethylenic unsaturation without a carboxylic function chosen from among the esters, amides or nitriles of acrylic and methacrylic acids, such as the acrylates or methacrylates or methyl, ethyl, butyl, 2-ethyl-hexyl, or from among acrylonitrile, vinyl acetate, styrene, methylstyrene, diisobutylene, vinylpyrrolidone, vinylcaprolactame, c) 2 to 25%, and preferentially 5 to 20%, of at least one monomer with ethylenic unsaturation and terminated by a hydrophobic and non-aromatic branched chain with 10 to 24 carbon atoms, having the following formula:

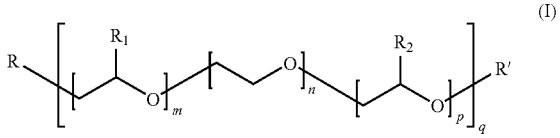

where:

m and p represent a number of alkylene oxide units of between 0 and 150, n represents a number of ethylene oxide units of between 5 and 150, q represents a whole number at least equal to 1 and such that $5 \leqq (m+n+p)q \leqq 150$, and preferentially such that $15 \leqq (m+n+p)q \leqq 120$, $R_1$ represents the methyl or ethyl radical, $R_2$ represents the methyl or ethyl radical, R represents a radical containing a polymerisable unsaturated function belonging to the group of acrylic, methacrylic, maleic, itaconic or crotonic esters, R' represents a hydrophobic and non-aromatic branched chain with 10 to 24 carbon atoms.

d) 0% to 3% of at least one monomer with at least two ethylenic unsaturations chosen from the group consisting of ethylene glycol diacrylate, ethylene glycol dimethacrylate, trimethylolpropanetriacrylate, trimethylolpropanetrimethacrylate, allyl acrylate, methylenebisacrylamide, methylenebismethacrylamide, tetrallyloxyethane, the triallylcyanurates, the allylic ethers obtained from polyols chosen from among pentaerythritol, sorbitol, or again sucrose, where the total by weight of the monomers a), b), c) and d) is equal to 100%.

In a preferential manner, this copolymer used according to the invention as a thickening agent is characterised in that it contains, expressed by weight, 2 to 25%, and preferentially 5 to 20%, of at least one oxyalkylated monomer with ethylenic unsaturation and terminated by a hydrophobic and non-aromatic branched chain with 12 to 24 carbon atoms, and having 2 branchings with at least 6 carbon atoms.

In a preferential manner, this copolymer thickening agent is characterised in that it contains, expressed by weight, 2 to 25%, and preferentially 5 to 20%, of at least one oxyalkylated monomer with ethylenic unsaturation and terminated by a hydrophobic and non-aromatic branched chain with 16 to 20 carbon atoms, and having 2 branchings with at least 6 carbon atoms.

In an even more preferential manner, the hydrophobic non-aromatic branched chain of the monomer c) is chosen from among 2-hexyl 1-decanyl and 2-octyl 1-dodecanyl.

In an equally preferential variant, this copolymer does not contain the crosslinking monomer d).

This copolymer is also characterised in that it is in its acid form, or partially or totally neutralised by one or more neutralisation agents having a monovalent neutralising function, such as those chosen from the group constituted by the alkaline cations, in particular sodium, potassium, lithium, ammonium or the aliphatic and/or cyclic primary, secondary, tertiary amines such as stearylamine, the ethanolamines (mono-, di- or tri-ethanolamine), mono- di-ethylamine, cyclohexylamine, methylcyclohexylamine, 2-amino 2-methyl 1-propanol and morpholine.

This water-soluble acrylic copolymer is obtained by the copolymerisation techniques well known to the skilled man in the art, such as the techniques of radical copolymerisation in solution, in a direct or reverse emulsion, in suspension, or precipitation in appropriate solvents, in the presence of catalytic systems and known transfer agents Another object of the invention also concerns the process of manufacture of possibly pigmented aqueous formulations characterised in that the said copolymer is added to the said formulations in the presence of compounds, whether or not water-soluble, such as salts or surfactants, or when the said compounds are added to the said aqueous formulations.

A final object of the invention concerns, lastly, possibly pigmented aqueous formulations containing these said copolymers, such as coating formulations such as paints in their aqueous phase, and notably dispersion paints, varnishes, paper coatings, cosmetics, detergence, textile formulations and drilling muds, or again plaster formulations, formulations for plasterboard, for hydraulic binders such as mortar formulations, or again formulations for ceramics and for leather.

The following examples illustrate the invention without however limiting its scope.

EXAMPLE 1

This example illustrates the use of copolymers according to the invention in aqueous paint formulations, and seeks to highlight the pigmentary compatibility Theological properties contributed by the copolymers according to the invention for formulations for matt paint in the aqueous phase, and with a constant dosage.

Thus, starting with a matt decoration paint formulation in aqueous phase with a vinyl-acrylic dispersion binder base, "UCAR™ latex 300" from Dow, the formula of which is shown in table 1, the aim consisted in checking in this formula the pigmentary compatibility (or compatibility provided with the addition of universal pigmentary concentrates), as influenced by different associative acrylic thickening agents, including thickening agents of the prior art, the hydrophobic groupings of which are linear, and thickening agents according to the invention, the hydrophobic groupings of which are branched.

TABLE 1

PAINT FORMULA

| Compounds | Role | Quantity (gram) |
|---|---|---|
| Water | Vehicle | 2639 |
| Cellosize ™ HEC ER-4400 | Cellulosic thickening agent | 13 |
| Potassium tripolyphoshate | Dispersing agent | 19.5 |
| Tamol ™ 1124 | Dispersing agent | 65 |
| Triton ™ CF-10 | Surfactant | 39 |
| Hi-Mar ™ DFC-19 | Anti-foaming agent | 26 |
| Kathon ™ LX (1.5%) | Biocide | 19.5 |
| Carbonate de sodium | Neutralising agent | 46.8 |
| TiPure ™ R-900 | Titanium dioxide | 2340 |
| Huber ™ 70 C | Calcinated clay | 2906.8 |
| Snowhite ™ 12 | Calcium carbonate | 1300 |
| Nyad ™ 400 | Wollastonite | 260 |
| Water | Vehicle | 936 |
| Ucar ™ Latex 300 | Binder | 2600 |
| Hi-Mar ™ DFC-19 | Anti-foaming agent | 26 |
| Water | Final diluent | 2207.4 |

To do so in each test, the above-mentioned matt paint formulation was prepared, and 0.3% by dry weight relative to the total weight of the white paint formula (but before addition of the universal pigmentary concentrate) of the thickening agent for testing was added to it, and then 36 millilitres of the universal pigmentary concentrate (of the Colortrend™ M 888 type from the company Hüls/Creanova) was added on to a kilogram of a white paint base which had been previously thickened with one of the associative acrylic thickening agents.

Two used universal pigmentary concentrates were chosen from the Colortrend™ M 888 range in order to represent the main families of organic pigments: phtalocyanine blue and quinacridone magenta.

At this stage, as limited as possible a reduction or an increase (relative to the white base) of the Stormer™ viscosity expressed in Krebs Units (KU) reflects a satisfactory compatibility with the universal pigmentary concentrate.

This Stormer™ viscosity test is used by the skilled man in the art as a selection test enabling them to eliminate formulations posing problems of compatibility with universal pigmentary concentrates.

Indeed, the skilled man in the art appreciates in particular that the Stormer™ viscosity, which is a viscosity with an average velocity gradient perceptible by the client (stirring with a spatula or brush, painting with a brush or roller), should be changed as little as possible by this addition of universal pigmentary concentrate.

Test n° 1:
This test illustrates the prior art and uses 0.3% by dry weight of a copolymer consisting of:
a) 37.2% methacrylic acid,
b) 52.8% of ethyl acrylate,
c) 10.0% of the monomer of formula (I), where
R represents a methacrylate radical,
R' represents a linear hydrophobic chain with 16 carbon atoms,
$m=p=0$,
$q=1$,
$n=25$.

Test n° 2:
This test illustrates the invention and uses 0.3% by dry weight of a copolymer consisting of:
a) 37.2% methacrylic acid,
b) 52.8% of ethyl acrylate,
c) 10.0% of the monomer of formula (I), where
R represents a methacrylate radical,
R' represents the non-aromatic hydrophobic chain with 16 carbon atoms 2-hexyl 1-decanyl,
$m=p=0$,
$q=1$,
$n=25$.

Test n° 3:
This test illustrates the prior art and uses 0.3% by dry weight of a copolymer consisting of:
a) 37.3% methacrylic acid,
b) 52.6% of ethyl acrylate,
c) 10.1% of the monomer of formula (I), where
R represents a methacrylate radical,
R' represents a linear hydrophobic chain with 16 carbon atoms,
$m=p=0$,
$q=1$,
$n=25$ and obtained by use of 0.05% by weight of dodecylmercaptan relative to the weight of the monomers.

Test n° 4:
This test illustrates the invention and uses 0.3% by dry weight of a copolymer consisting of:
a) 37.3% methacrylic acid,
b) 52.6% of ethyl acrylate,
c) 10.1% of the monomer of formula (I), where
R represents a methacrylate radical,
R' represents the non-aromatic hydrophobic chain with 16 carbon atoms 2-hexyl 1-decanyl,
$m=p=0$,
$q=1$,
$n=25$ and obtained by use of 0.05% by weight of dodecylmercaptan relative to the weight of the monomers.

Test n° 5:
This test illustrates the prior art and uses 0.3% by dry weight of a copolymer consisting of:
a) 43.5% methacrylic acid,
b) 47.6% of ethyl acrylate,
c) 8.9% of the monomer of formula (I), where
R represents a methacrylate radical,
R' represents a linear hydrophobic chain with 16 carbon atoms,
$m=p=0$,
$q=1$,
$n=25$ and obtained by use of 0.30% by weight of dodecylmercaptan relative to the weight of the monomers.

Test n° 6:
This test illustrates the invention and uses 0.3% by dry weight of a copolymer consisting of:
a) 43.5% methacrylic acid,
b) 47.6% of ethyl acrylate,
c) 8.9% of the monomer of formula (I), where
R represents a methacrylate radical,
R' represents the non-aromatic hydrophobic chain with 16 carbon atoms 2-hexyl 1-decanyl,
$m=p=0$,
$q=1$,
$n=25$ and obtained by use of 0.30% by weight of dodecylmercaptan relative to the weight of the monomers.

Test n° 7:
This test illustrates the prior art and uses 0.3% by dry weight of a copolymer consisting of:
a) 36.7% methacrylic acid,
b) 53.1% of ethyl acrylate,
c) 10.2% of the monomer of formula (I), where
R represents a methacrylate radical,
R' represents a linear hydrophobic chain with 20 carbon atoms,
$m=p=0$,
$q=1$,
$n=25$.

Test n° 8:
This test illustrates the invention and uses 0.3% by dry weight of a copolymer consisting of:
a) 36.7% methacrylic acid,
b) 53.1% of ethyl acrylate,
c) 10.2% of the monomer of formula (I), where
R represents a methacrylate radical,
R' represents the non-aromatic hydrophobic chain with 20 carbon atoms 2-octyl 1-dodecanyl, m=p=0,
q=1,
n=25.

Test n° 9:

This test illustrates the prior art and uses 0.3% by dry weight of a copolymer consisting of:
a) 36.7% methacrylic acid,
b) 53.1% of ethyl acrylate,
c) 10.2% of the monomer of formula (I), where
R represents a methacrylate radical,
R' represents a linear hydrophobic chain with 20 carbon atoms,
m=p=0,
q=1,
n=25 and obtained by use of 0.05% by weight of dodecylmercaptan relative to the weight of the monomers.

Test n° 10:

This test illustrates the invention and uses 0.3% by dry weight of a copolymer consisting of:
a) 36.7% methacrylic acid,
b) 53.1% of ethyl acrylate,
c) 10.2% of the monomer of formula (I), where
R represents a methacrylate radical,
R' represents the non-aromatic hydrophobic chain with 20 carbon atoms 2-octyl 1-dodecanyl,
m=p=0,
q=1,
n=25 and obtained by use of 0.05% by weight of dodecylmercaptan relative to the weight of the monomers.

All the results are shown in the following table 2.

TABLE 2

| Test n° | PA or INV | Stormer™ viscosity (KU) of the White base | After addition of blue colorant | Delta KU with blue colorant | After addition of magenta colorant | Delta KU with magenta colorant |
|---|---|---|---|---|---|---|
| 1 | PA | 120 | 125.6 | 5.6 | 131.8 | 11.8 |
| 2 | INV | 95.1 | 97.9 | 2.8 | 103.8 | 8.7 |
| 3 | PA | 127.1 | 132.2 | 5.1 | 133.2 | 6.1 |
| 4 | INV | 97.9 | 101 | 3.1 | 103.5 | 5.6 |
| 5 | PA | 101.8 | 95.9 | 5.9 | 105 | 3.2 |
| 6 | INV | 60.1 | 61.1 | 1 | 60.9 | 0.8 |
| 7 | PA | 107.4 | 119 | 11.6 | 117.8 | 10.4 |
| 8 | INV | 102.7 | 111 | 8.3 | 109.8 | 7.1 |
| 9 | PA | 105.5 | 114.4 | 8.9 | 116.1 | 10.6 |
| 10 | INV | 111.9 | 117.2 | 5.3 | 119.7 | 7.8 |

PA = Prior Art,
INV = Invention.

In all cases, the variation of the absolute value of the Stormer™ viscosity of the paints after addition of the colorants is smaller with the paints containing the thickening agents according to the invention, compared to that of the paints containing the corresponding thickening agents of the prior art.

EXAMPLE 2

This example illustrates the use of copolymers according to the invention in the field of drilling fluids, and particularly that of synthetic muds, and seeks to highlight the maintenance of the thickening conferred by the copolymers according to the invention for formulations with a constant dosage by dry weight of thickening agent.

In the field of drilling fluids, and particularly of synthetic muds, the skilled man in the art may be induced to use a mud consisting solely of a thickening agent and of water, in order to reduce the quantity of non-recyclable matter. These muds must have a suspensivant power which, although becoming reduced during pumping, must remain relatively high under stress conditions, such as the passage of the fluid in the annular space when debris is brought up. Traditional muds based on thickening agents of the prior art have the defect that they are too pseudoplastic, i.e. lose most of their viscosity when subjected to shearing. This phenomenon is easily measured by calculating the ratio of the Brookfield™ viscosities measured at 100 RPM to the Brookfield™ viscosities measured at 10 RPM. A low figure is an indication of a substantial reduction of viscosity under shearing.

A comparison of the various polymers was made by making aqueous gels of these products at concentrations such that the Brookfield™ viscosities obtained are situated between 1000 mPa·s and 5000 mPa·s at 10 RPM. The pHs of these gels were all adjusted to 8.

Test n° 11:

This test illustrates the prior art and uses 1% by dry weight of a copolymer consisting of:
a) 37.2% methacrylic acid,
b) 52.8% of ethyl acrylate,
c) 10.0% of the monomer of formula (I), where
R represents a methacrylate radical,
R' represents a linear hydrophobic chain with 16 carbon atoms,
m=p=0,
q=1,
n=25.

Test n° 12:

This test illustrates the invention and uses 1% by dry weight of a copolymer consisting of:
a) 37.2% methacrylic acid,
b) 52.8% of ethyl acrylate,
c) 10.0% of the monomer of formula (I), where
R represents a methacrylate radical,
R' represents the non-aromatic hydrophobic chain with 16 carbon atoms 2-hexyl 1-decanyl,
m p=0,
q=1,
n=25.

Test n° 13:

This test illustrates the prior art and uses 1% by dry weight of a copolymer consisting of:
a) 42.83% methacrylic acid,
b) 52.97% of ethyl acrylate,
c) 2.66% of the monomer of formula (I), where
R represents a methacrylate radical,
R' represents a linear hydrophobic chain with 16 carbon atoms,
m=p=0,
q=1,
n=25,
d) 1.54% ethylene glycol dimethacrylate.

Test n° 14:

This test illustrates the invention and uses 1% by dry weight of a copolymer consisting of:
a) 42.83% methacrylic acid,
b) 52.97% of ethyl acrylate, c) 2.66% of the monomer of formula (I), where
  R represents a methacrylate radical,
  R' represents the non-aromatic hydrophobic chain with 16 carbon atoms 2-hexyl 1-decanyl,
  m=p=0,
  q=1,
  n=25,
d) 1.54% ethylene glycol dimethacrylate.

Test n° 15:
This test illustrates the prior art and uses 1% by dry weight of a copolymer consisting of:
a) 43.5% methacrylic acid,
b) 47.6% of ethyl acrylate,
c) 8.9% of the monomer of formula (I), where
  R represents a methacrylate radical,
  R' represents a linear hydrophobic chain with 16 carbon atoms,
  m=p=0,
  q=1,
  n=25 and obtained by use of 0.30% by weight of dodecylmercaptan relative to the weight of the monomers.

Test n° 16:
This test illustrates the invention and uses 1% by dry weight of a copolymer consisting of:
a) 43.5% methacrylic acid,
b) 47.6% of ethyl acrylate,
c) 8.9% of the monomer of formula (I), where
  R represents a methacrylate radical,
  R' represents the non-aromatic hydrophobic chain with 16 carbon atoms 2-hexyl 1-decanyl,
  m=p=0,
  q=1,
  n=25 and obtained by use of 0.30% by weight of dodecylmercaptan relative to the weight of the monomers.

Test n° 17:
This test illustrates the prior art and uses 1% by dry weight of a copolymer consisting of:
a) 36.7% methacrylic acid,
b) 53.1% of ethyl acrylate,
c) 10.2% of the monomer of formula (I), where
  R represents a methacrylate radical,
  R' represents a linear hydrophobic chain with 20 carbon atoms,
  m=p=0,
  q=1,
  n=25 and obtained by use of 0.30% by weight of dodecylmercaptan relative to the weight of the monomers.

Test n° 18:
This test illustrates the invention and uses 1% by dry weight of a copolymer consisting of:
a) 36.7% methacrylic acid,
b) 53.1% of ethyl acrylate,
c) 10.2% of the monomer of formula (I), where
  R represents a methacrylate radical,
  R' represents the non-aromatic hydrophobic chain with 20 carbon atoms 2-hexyl 1-decanyl,
  m=p=0,
  q=1,
  n=25 and obtained by use of 0.30% by weight of dodecylmercaptan relative to the weight of the monomers.

Test n° 19:
This test illustrates the prior art and uses 1% by dry weight of a copolymer consisting of:
a) 42.68% methacrylic acid,
b) 53.12% of ethyl acrylate,
c) 2.66% of the monomer of formula (I), where
  R represents a methacrylate radical,
  R' represents a linear hydrophobic chain with 16 carbon atoms,
  m=p=0,
  q=1,
  n=25,
d) 1.54% ethylene glycol dimethacrylate.

Test n° 20:
This test illustrates the invention and uses 1% by dry weight of a copolymer consisting of:
a) 42.68% methacrylic acid,
b) 53.12% of ethyl acrylate,
c) 2.66% of the monomer of formula (I), where
  R represents a methacrylate radical,
  R' represents the non-aromatic hydrophobic chain with 16 carbon atoms 2-hexyl 1-decanyl,
  m=p=0,
  q=1,
  n=25,
d) 1.54% ethylene glycol dimethacrylate.

Test n° 21:
This test illustrates the prior art and uses 1% by dry weight of a copolymer consisting of:
a) 34.2% methacrylic acid,
b) 60.4% of ethyl acrylate,
c) 5.4% of the monomer of formula (I), where
  R represents a methacrylate radical,
  R' represents a linear hydrophobic chain with 20 carbon atoms,
  m=p=0,
  q=1,
  n=25 and obtained by use of 0.30% by weight of dodecylmercaptan relative to the weight of the monomers.

Test n° 22:
This test illustrates the invention and uses 1% by dry weight of a copolymer consisting of:
a) 34.2% methacrylic acid,
b) 60.4% of ethyl acrylate,
c) 5.4% of the monomer of formula (I), where
  R represents a methacrylate radical,
  R' represents the non-aromatic hydrophobic chain with 20 carbon atoms 2-octyl 1-dodecanyl,
  m=p=0,
  q=1,
  n=25 and obtained by use of 0.30% by weight of dodecylmercaptan relative to the weight of the monomers.

All the results are shown in the following table 3.

TABLE 3

|  | Brookfield ™ viscosity at 20° C., for 1% of dry matter | | Ratio of viscosity at 100 RPM over viscosity at 10 RPM of the |
|---|---|---|---|
| Tests n° | 10 RPM | 100 RPM | values for 1% of dry matter |
| 11 | 9,455 | 1,709 | 0.181 |
| 12 | 3,429 | 2,386 | 0.696 |
| 13 | 6,000 | 1,293 | 0.216 |
| 14 | 4,660 | 1,097 | 0.235 |
| 15 | 1,818 | 1,536 | 0.845 |
| 16 | 460 | 452 | 0.983 |
| 17 | 10,000 | 1,600 | 0.160 |
| 18 | 8,226 | 2,194 | 0.267 |
| 19 | 7,619 | 1,270 | 0.167 |
| 20 | 7,333 | 1,600 | 0.218 |
| 21 | 6,500 | 3,825 | 0.588 |
| 22 | 2,727 | 2,848 | 1.044 |

Table 3 above perfectly illustrates the clear superiority of the polymers according to the invention compared to the polymers of the prior art, since the ratio of the Brookfield™ viscosities measured at 100 RPM over the Brookfield™ viscosities measured at 10 RPM are, respectively, much higher for the tests illustrating the invention.

EXAMPLE 3

This example illustrates the use of copolymers according to the invention in the field of detergence and cosmetics, and seeks to highlight the maintenance of the thickening conferred by the copolymers according to the invention for formulations with a constant dosage by dry weight of thickening agent, despite the addition of salts.

Both in the previous application (drilling muds) and in a cosmetic or detergence application, the presence of salt is sometimes unavoidable or inevitable. Indeed, synthetic drilling muds can be manufactured from seawater or, being manufactured from fresh water, can be brought into contact with saline geological strata. It is important that the viscosity of the mud should resist this contamination in order to guarantee its effectiveness in bringing up debris during the drilling. Similarly, many cosmetic or detergent formulations contain salts, used among other things as viscosity exhausters in relation to surfactants, in addition to thickening agents; it is therefore important that the said thickening agents should resist the addition of salts. The comparison of the various polymers was made by making aqueous gels of these products at concentrations such that the Brookfield™ viscosities obtained are situated between 1000 and 5000 mPa·s at 10 RPM. The pHs of these gels were all adjusted to 8. After measurement of the Brookfield™ viscosities, quantities of sodium chloride corresponding to 1 and 2% of the formulation were added and dissolved. The Brookfield™ viscosities were then measured again.

Test n° 23:
This test illustrates the prior art and uses 1% by dry weight of the copolymer used in test n° 11.

Test n° 24:
This test illustrates the invention and uses 1% by dry weight of the copolymer used in test n° 12.

Test n° 25:
This test illustrates the prior art and uses 1% by dry weight of the copolymer used in test n° 17.

Test n° 26:
This test illustrates the invention and uses 1% by dry weight of the copolymer used in test n° 18.

Test n° 27:
This test illustrates the prior art and uses 1% by dry weight of the copolymer used in test n° 21.

Test n° 28:
This test illustrates the invention and uses 1% by dry weight of the copolymer used in test n° 22.

All the results are shown in the following table 4.

TABLE 4

|  | Brookfield ™ viscosity 10 T at 20° C. at 1% of dry matter | | |
|---|---|---|---|
| Test n° | Without salt | 1% NaCl | 2% NaCl |
| 23 | 9,455 | 727 | 73 |
| 24 | 3,429 | 4,929 | 3,000 |
| 25 | 10,000 | 360 | 80 |
| 26 | 8,226 | 1,129 | 129 |
| 27 | 6,500 | 150 | 25 |
| 28 | 2,727 | 848 | 121 |

Table 4 above illustrates perfectly the superiority of the polymers according to the invention compared to the polymers of the prior art.

EXAMPLE 4

This example illustrates the use of copolymers according to the invention in the field of detergence and cosmetics, and seeks to highlight the development of the thickening conferred by the copolymers according to the invention for formulations with a constant dosage by dry weight of thickening agent, despite the addition of surfactants.

Detergent and cosmetic formulations contain one or more ionic and non-ionic surfactants. The skilled man in the art has constantly used combinations of the solublising/insolubilising properties of these pairs of surfactants to thicken the formulations containing them. The thickening polymers to be found in the market now enable the quantities of surfactants to be reduced appreciably, and the latter are now used only for their detergent properties. Use of the polymers according to the invention enables the viscosity of the formulations containing them to be improved significantly compared to the thickening polymers of the prior art. The comparison of the polymers was made by the production of aqueous formulations containing 11% of sodium lauryl alkylsulfate and 9% of cocoamidopropyl betaine. The pH of the formulations was adjusted to 8 using triethanolamine. The viscosity of the blend of surfactants without thickening agent is 20 mPa·s at 10 RPM.

Test n° 29:
This test illustrates the prior art and uses 1% by dry weight of the copolymer used in test n° 11.

Test n° 30:
This test illustrates the invention and uses 1% by dry weight of the copolymer used in test n° 12.

Test n° 31:
This test illustrates the prior art and uses 1% by dry weight of the copolymer used in test n° 19.

Test n° 32:

This test illustrates the invention and uses 1% by dry weight of the copolymer used in test n° 20.

Test n° 33:

This test illustrates the prior art and uses 1% by dry weight of the copolymer used in test n° 21.

Test n° 34:

This test illustrates the invention and uses 1% by dry weight of the copolymer used in test n° 22.

All the results are shown in the following table 5.

TABLE 5

| Tests n° | Brookfield ™ viscosity for 1% of dry matter | |
|---|---|---|
| | 10 RPM | 100 RPM |
| 29 | 20,000 | 17,455 |
| 30 | 27,143 | 18,143 |
| 31 | 444 | 495 |
| 32 | 867 | 853 |
| 33 | 750 | 744 |
| 34 | 2,303 | 2,109 |

Table 5 above illustrates perfectly the superiority of the polymers according to the invention compared to the polymers of the prior art

EXAMPLE 5

This example illustrates the use of copolymers according to the invention in the field of paper coatings, and seeks to highlight the maintenance of the thickening conferred by the copolymers used according to the invention for formulations with a constant dosage by dry weight of thickening agent despite the addition of salts.

To accomplish this, for each of the tests the thickening agent to be tested is added to a paper coating consisting of 100 parts of an aqueous suspension of calcium carbonate at a rate of 78% of dry matter, sold by the company Omya™ under the name Hydrocarb™ 60, and of 10 parts of latex at a rate of 50% of dry matter, sold by the company Dow under the name DL 940, and then, after 15 minutes' stirring, the Brookfield™ viscosity at 100 revolutions per minute is measured, using a Brookfield™ viscometer fitted with the appropriate module.

Once the Brookfield™ viscosity at 100 revolutions per minute has been determined, for each of the tests 1.6 parts of powdery sodium chloride is added, and then, after 15 minutes' stirring, the Brookfield™ viscosity is measured at 100 revolutions per minute using a Brookfield™ viscometer fitted with the appropriate module.

Test n° 35:

This test illustrates the prior art and uses the copolymer used in test n° 11.

The Brookfield™ viscosities at 100 revolutions per minute obtained are:

Before addition of the sodium chloride: 3100 mPa·s

After addition of the sodium chloride: 2400 mPa·s

Test n° 36:

This test illustrates the invention and uses the copolymer used in test n° 12.

The Brookfield™ viscosities at 100 revolutions per minute obtained are:

Before addition of the sodium chloride: 2700 mPa·s

After addition of the sodium chloride: 3020 mPa·s

A reading of the results of the previous two tests shows the superiority of the polymers according to the invention.

EXAMPLE 6

This example illustrates the use of copolymers according to the invention in the field of plaster.

For tests n° 37 and n° 38, a formulation of joint filler for plasterboard was produced, respectively with a product of the prior art which is a methacrylic/ethyl acrylate acidic copolymer, and a copolymer consisting of:

a) 34.6% of methacrylic acid, b) 56.1% of ethyl acrylate, c) 9.3% of the monomer of formula (I) designated mono I" and in which mono I" designates a monomer of formula (I) in which:

R represents a methacrylate radical,

R' represents the non-aromatic hydrophobic chain with 20 carbon atoms: 2-octyl 1-dodecanyl, m=p=0, q=1, n=25

The composition of the formulations is given in table 6, and the said formulations are produced by the addition of the constituents, in the order of the table, whilst being stirred in a planetary mixer.

After the blend is produced, the Brookfield™ viscosity of the formulation at 10 revolutions/minute is measured at instants t=0 and t=24 hours, according to the methods well known by the skilled man in the art.

TABLE 6 composition (by weight) of the plaster formulations according to the prior art (test n° 37) and according to the invention (test n° 38) and corresponding Brookfield ™ viscosities at 10 revolutions/minute measured at t = 0 and t = 24 hours

| Constituents | Test n° 37 prior art | Test n° 38 invention |
|---|---|---|
| Ordinary water | 253.5 g | 253.5 g |
| Drewplus ™ L475 anti-foaming agent (sold by DREW ™) | 0.12 g | 0.12 g |
| Biocide Acticide ™ MBS (sold by THOR ™) | 0.23 g | 0.23 g |
| Methacrylic acid/ethyl acrylate copolymer | 7.7 g | 0 |
| Copolymer of test n° 38 | 0 | 7.7 g |
| Sodium hydroxide (50% solution) | 1.25 | 1.25 |
| Mica MICA-MU 280 (sold by Comptoir de Minéraux et Matières Premières) | 30 g | 30 g |
| Millwhite Attapulgite Clay (sold by Millwhite Company, Inc.) | 20 g | 20 g |
| Ordinary water | 42 g | 42 g |
| Pulpro 20 calcium carbonate (sold by OMYA ™) | 545 g | 545 g |
| Monopropylene Glycol | 1.5 g | 1.5 g |
| Polyvinyl acetate emulsion (sold by NACAN ™) | 35 g | 35 g |
| Sodium hydroxide 50% | 0.4 g | 0.4 g |
| Brookfield ™ viscosity (at 10 rev./minute) t = 0 | 101,000 mPa · s | 110,000 mPa · s |
| t = 24h00 | 95,000 mPa · s | 111,000 mPa · s |

Use of the copolymer according to the invention enables an initial viscosity greater than that obtained with the polymer of the prior art to be obtained, and this viscosity to be maintained over time.

EXAMPLE 7

This example illustrates the use of copolymers according to the invention in the field of cosmetics.

For tests n° 39 and n° 40, a skin moisturising formulation is produced, the composition and order of introduction of the constituents of which is given in table 7.

Tests n° 39 and n° 40 use respectively a thickening agent according to the prior art, which is a methacrylic/ethyl acrylate acidic copolymer, and a copolymer consisting of:

a) 36.5% of methacrylic acid, b) 44.1% of ethyl acrylate, c) 10.0% of butyl acrylate, d) 9.4% of the monomer of formula (I) designated mono I' and in which mono I' designates a monomer of formula (I) in which:

R represents a methacrylate radical,
R' represents the non-aromatic hydrophobic chain with 16 carbon atoms: 2-hexyl 1-decanyl,
$m=p=0$,
$q=1$,
$n=25$

TABLE 7 composition (weight in grams) of the cosmetic formulations according to tests n° 39 and n° 40

| INCI names<br>(International Nomenclature<br>Cosmetic Ingredient) | | Brand names/<br>Manufacturer |
|---|---|---|
| Phase A | | |
| Demineralised water | 57.02 | |
| EDTA disodium salt | 0.05 | |
| Monopropylene Glycol | 5 | |
| Phase B | | |
| Thickening agent<br>(according to prior art: test n° 39<br>according to the invention, test n° 40) | 2.13 | |
| Phase C | | |
| PEG-6 stearate, ceteth-20, glyceryl stearate, steareth-20, stearic acid | 11 | Tefose 2561/<br>GATTEFOSSÉ ™ |
| Octyldodecyl myristate | 9 | Pelemol 2014/PHOENIX ™<br>CHEMICAL INC. |
| Cyclomethicone | 6 | Dow Corning 345 Fluid/DOW<br>CORNING ™ |
| Sweet almond oil | 3 | Cropure Almond/CRODA ™ |
| Phase D | | |
| Demineralised water | 5 | |
| Phase E | | |
| TEA 99% | 0.34 | |
| Phase F | | |
| phenoxyethanol methylparaben butylparaben ethylparaben propylparaben | 1 | Phenonip/CLARIANT ™ |

Phase B is added to phase A which has been previously homogenised.

Simultaneously, phase C is homogenised, raising its temperature to 70° C. whilst stirring.

Homogenised phases A+B have their temperatures raised to 70° C. and blended into phase C.

The blend of phases A+B+C is cooled whilst stirring from 70° C. to 60° C., and then without stirring from 60° C. to 30° C.

Phase D is then added whilst stirring to the blend of phases A+B+C cooled to 30° C.

The pH of the phases A+B+C+D is then adjusted to 6.8 with phase E.

Phase F is then added whilst stirring to the blend of phases A+B+C+D+E.

The Brookfield™ viscosities are measured 24 hours after preparation at 25° C., and are indicated in table 8.

TABLE 8

Brookfield ™ viscosity of the cosmetic formulations according to the prior art (test n° 39) and according to the invention (test n° 40)

| Measurement speed | Brookfield ™ viscosity for test n° 39 (prior art) | Brookfield ™ viscosity for test n° 40 (invention) |
|---|---|---|
| 2.5 rev./min. | 90,000 mPa · s | 156,000 mPa · s |
| 5 rev./min. | 56,000 mPa · s | 102,000 mPa · s |
| 10 rev./min. | 36,000 mPa · s | 70,000 mPa · s |
| 20 rev./min. | 20,750 mPa · s | 46,000 mPa · s |
| 50 rev./min. | 10,900 mPa · s | 29,000 mPa · s |
| 100 rev./min. | 6,900 mPa · s | 17,600 mPa · s |

Use of the copolymer according to the invention enables a viscosity appreciably higher than the polymer of the prior art to be obtained.

For tests n° 41 and n° 42, a shampoo formulation is produced, the composition and the order of introduction of the constituents of which is given in table 9 (the order of introduction is not fundamental, but by following the chronology the manufacture of the formula is facilitated).

Tests n° 41 (prior art) and n° 42 (invention) use respectively a thickening agent according to the prior art, which is a methacrylic/ethyl acrylate acidic copolymer, and a copolymer consisting of:

a) 31.5% of methacrylic acid, b) 5.0% of acrylic acid, c) 54.1% of ethyl acrylate, d) 9.4% of the monomer of formula (I) designated mono I'.

Once the blend is produced the Brookfield™ viscosity is measured at instants t=0 and t=24 hours. These results are shown in table 9.

TABLE 9 composition (by weight of the constituents) of the shampoo formulations according to the prior art (test n° 41) and according to the invention (test n° 42) and corresponding Brookfield ™ viscosities measured at t = 0 and t = 24 hours

| Constituents | Test n° 41 (prior art) | Test n° 42 (invention) |
|---|---|---|
| Thickening agent | 16 g | 16 g |
| Bipermuted water | 109 g | 109 g |
| Sodium Laureth Sulfate Texapoan NSO (COGNIS ™) | 60 g | 60 g |
| Sodium hydroxide 50% | 1.5 g | 1.5 g |

TABLE 9-continued composition (by weight of the constituents) of the shampoo
formulations according to the prior art (test n° 41) and according
to the invention (test n° 42) and corresponding Brookfield ™
viscosities measured at t = 0 and t = 24 hours

| Constituents | | Test n° 41 (prior art) | Test n° 42 (invention) |
|---|---|---|---|
| Brookfield ™ viscosity at t = 0 | 1 rev./min. | 11,500 mPa·s | 16,000 mPa·s |
| | 10 rev./min. | 2,650 mPa·s | 11,000 mPa·s |
| | 20 rev./min. | 1,775 mPa·s | 7,500 mPa·s |
| | 100 rev./min. | 765 mPa·s | 6,500 mPa·s |
| Brookfield ™ viscosity at t = 24 hours | 1 rev./min. | 11,000 mPa·s | 16,000 mPa·s |
| | 10 rev./min. | 2,600 mPa·s | 11,000 mPa·s |
| | 20 rev./min. | 1,750 mPa·s | 9,500 mPa·s |
| | 100 rev./min. | 780 mPa·s | 9,000 mPa·s |

Use of the copolymer according to the invention enables a viscosity higher than the polymer of the prior art to be obtained.

EXAMPLE 8

This example illustrates the use of copolymers according to the invention in the field of detergence.

For tests n° 43 and n° 44, a scouring cream formulation is produced, the composition and the order of introduction of the constituents of which is given in table 10 (the order of introduction is not fundamental, but by following the chronology the manufacture of the formula is facilitated).

Tests n° 43 (prior art) and n° 44 (invention) use respectively a thickening agent according to the prior art, which is a methacrylic/ethyl acrylate acidic copolymer, and a copolymer consisting of:

a) 31.5% of methacrylic acid, b) 5.0% of itaconic acid, c) 54.1% of ethyl acrylate, d) 9.4% of the monomer of formula (I) designated mono I'.

Once the blend is produced, the Brookfield™ viscosity is measured at instant t=0; the results are shown in table 10.

TABLE 10 composition (by weight of the constituents) of the scouring cream
formulations according to the prior art (test n° 43) and
according to the invention (test n° 44) and corresponding
Brookfield ™ viscosities measured at t = 0

| Constituents | | Test n° 43 (prior art) | Test n° 44 (invention) |
|---|---|---|---|
| Monoethanol amine | | 4 g | 4 g |
| Ethoxylated isotridecanol surfactant | | 2 g | 2 g |
| Perfume | | 0.4 g | 0.4 g |
| Calcium carbonate Omyacarb 30AV OMYA ™) | | 90 g | 90 g |
| Thickening agent | | 6 g | 6 g |
| Brookfield ™ viscosity at t = 0 | 1 rev./min. | 10,500 mPa·s | 30,000 mPa·s |
| | 10 rev./min. | 3,100 mPa·s | 25,500 mPa·s |
| | 20 rev./min. | 2,250 mPa·s | 25,000 mPa·s |
| | 100 rev./min. | 1,200 mPa·s | 16,000 mPa·s |

Use of the copolymer according to the invention enables a viscosity very much higher than the polymer of the prior art to be obtained.

EXAMPLE 9

This example illustrates the use of copolymers according to the invention in the field of liquid soaps.

Hand washing formulations increasingly use liquid soaps of natural or synthetic origin. Unlike certain surface active agents, these soaps often cannot be thickened using sodium chloride. For economic reasons they are often diluted and consequently lose all viscosity. In order to make them keep an appearance compatible with use, a thickening agent must be used as described in the following tests.

For tests n° 45 and n° 46, a liquid soap formulation is produced, the composition and the order of introduction of the constituents of which is given in table 11 (the order of introduction is not fundamental, but by following the chronology the manufacture of the formula is facilitated).

Tests n° 45 (prior art) and n° 46 (invention) use respectively a thickening agent according to the prior art, which is a methacrylic/ethyl acrylate acidic copolymer, and a copolymer consisting of:

a) 30.1% of methacrylic acid, b) 51.4% of ethyl acrylate, c) 18.5% of the monomer of formula (I) designated mono I'.

Once the blend has been produced, the soap is left undisturbed for 24 hours and the Brookfield™ viscosity is then measured at instant t=24 hours.

TABLE 11 composition (by weight of the constituents) of the liquid soaps
formulations according to the prior art (test n° 45)
and according to the invention (test n° 46) and
corresponding Brookfield ™ viscosities
measured at t = 24 hours

| Constituents | | Test n° 45 (prior art) | Test n° 46 (invention) |
|---|---|---|---|
| Ordinary water | | 100 g | 100 g |
| Copra soap 50% | | 100 g | 100 g |
| Thickening agent | | 6 g | 6 g |
| Potassium hydroxide 50% | | qsp pH 9.5 | qsp pH 9.5 |
| Brookfield ™ viscosity | 10 rev./min. | 80 mPa·s | 140 mPa·s |
| | 100 rev./min. | 84 mPa·s | 175 mPa·s |

Use of the copolymer according to the invention enables a viscosity higher than the polymer of the prior art to be obtained.

For tests n° 47 and n° 48, an alcoholic wash formulation is produced, the composition and the order of introduction of the constituents of which is given in table 12 (the order of introduction is not fundamental, but by following the chronology the manufacture of the formula is facilitated).

Certain washing formulations for floors must be effective, whilst leaving no traces even if no rinsing takes place. To this end, the skilled man in the art uses a blend of water, alcohol and surfactant. This formulation must be slightly thickened to be able to be used with ease.

Tests n° 47 (invention) and n° 48 (reference) use respectively a copolymer consisting of:

a) 32.1% of methacrylic acid, b) 55.3% of ethyl acrylate, c) 12.6% of the monomer of formula (I) designated mono I'.

and no thickening agent.

Once the blend is produced, the Brookfield™ viscosity is measured at instant t=0; the results are shown in table 12.

TABLE 12 composition (by weight of the constituents) of the alcoholic wash formulations according to the reference (test n° 48) and according to the invention (test n° 47) and corresponding Brookfield ™ viscosities measured at t = 0

| Constituents | Test n° 47 (invention) | Test n° 48 (reference) |
|---|---|---|
| Denatured ethanol | 45 g | 45 g |
| Bipermuted water | 105 g | 105 g |
| Thickening agent | 5 g | 0 g |
| Ethoxylated fatty alcohol polyglycol (8 EO) ZUZOLAT 1008/25 (ZSCHIMMER & SCHWARZ ™) | 2 g | 2 g |
| Triethanolamine | qsp pH 8.0 | qsp pH 8.0 |
| Brookfield ™ viscosity (10 rev./min.) | 140 mPa · s | 20 mPa · s |

Use of the copolymer according to the invention enables the formulation according to the invention to be thickened appreciably.

EXAMPLE 10

This example illustrates the use of copolymers according to the invention in the textile field.

For tests n° 49 and n° 50, a textile printing paste is produced, the composition and the order of introduction of the constituents of which is given in table 13 (the order of introduction is not fundamental, but by following the chronology the manufacture of the formula is facilitated).

Tests n° 49 (invention) and n° 50 (reference) use respectively a thickening agent which is a copolymer consisting of:

a) 34.5% of methacrylic acid, b) 56.1% of ethyl acrylate, c) 9.4% of the monomer of formula (I) designated mono I'.

and no thickening agent.

Once the blend is produced, the Brookfield™ viscosity is measured at instant t=0; the results are shown in table 13.

TABLE 13 composition (by weight of the constituents) of the textile printing pastes according to the reference (test n° 50) and according to the invention (test n° 49) and corresponding Brookfield ™ viscosities measured at t = 0

| Consituents | | Test n° 49 (invention) | Test n° 50 (reference) |
|---|---|---|---|
| Water | | 212.2 g | 212.2 g |
| Anti-foaming agent Bubblex 250 (COGNIS ™) | | 1 g | 1 g |
| Acrylic emulsion for textile printing paste | | 30.8 g | 30.8 g |
| Ammonia 28% | | qsp pH 8-8.5 | qsp pH 8-8.5 |
| Thickening agent | | 6 g | 0 g |
| Brookfield ™ viscosity at t = 0 | 1 tour/min. | 1,000 mPa · s | 20 mPa · s |
| | 10 rev./min. | 300 mPa · s | 20 mPa · s |
| | 20 rev./min. | 250 mPa · s | 20 mPa · s |
| | 100 rev./min. | 200 mPa · s | 20 mPa · s |

Use of the copolymer according to the invention enables the formulation to be thickened notably.

EXAMPLE 11

This example illustrates the use of copolymers according to the invention in the field of ceramics.

In this example, a formulation is produced called an enamelling vehicle because it is used as a carrier for the enamelling of ceramics such as, in a non-restrictive manner, tiles and sanitary items. This formulation will be used by the skilled man in the art as a liquid in which powdered enamels will be dispersed and then possibly ground. The addition of a thickening agent allows a satisfactory final viscosity to be obtained enabling both an easy application and a stabilisation of the enamel dispersion during storage.

For tests n° 51 and n° 52, an enamelling vehicle formulation is produced, the composition and the order of introduction of the constituents of which is given in table 14 (the order of introduction is not fundamental, but by following the chronology the manufacture of the formula is facilitated).

Tests n° 51 (prior art) and n° 52 (invention) use respectively a thickening agent according to the prior art, which is a methacrylic/ethyl acrylate acidic copolymer, and a copolymer consisting of:

a) 36.5% of methacrylic acid, b) 44.1% of ethyl acrylate, c) 10.0% of vinyl acetate, d) 9.4% of the monomer of formula (J) designated mono I'.

Once the blend has been produced the viscosity of the formulation is measured using a Ford cup fitted with a 4 mm orifice, according to the methods well known to the skilled man in the art.

The composition of the formulations and the viscosity values obtained are indicated in table 14.

TABLE 14 cpmposition (by weight of constituents) for tests n° 51 (prior art) and n° 52 (invention) and Ford cup viscosities obtained

| Constituents | Test n° 51 (prior art) | Test n° 52 (invention) |
|---|---|---|
| Ordinary water | 101.1 g | 101.1 g |
| Bubblex ™ 250 anti-foaming agent (COGNIS ™) | 1.2 g | 1.2 g |
| Thickening agent | 5 g | 5 g |
| Sodium hydroxide 50% | 0.5 g | 0.5 g |
| Monopropylene glycol | 90 g | 90 g |
| Coatex ™ DV 204 dispersing agent (COATEX ™) | 2 g | 2 g |
| Ford Cup viscosity, diameter 4 | 16 seconds | 20 seconds |

Use of the copolymer according to the invention enables a viscosity higher than that resulting from use of the polymer according to the prior art to be obtained.

For tests n° 53 and n° 54, slip formulations are produced which are used in the ceramics field.

The manufacture of ceramic parts and materials makes use of dispersions of various ground clays and minerals in the aqueous phase. In the case of certain parts, the ground dispersion of these minerals, called slip, may be kept in a liquid form to be used by moulding or casting. Although certain applications require a slip of low viscosity, others require a higher viscosity in order either to keep the mineral particles in suspension, or to give the slip viscosity characteristics allowing its application by casting in a mould or in a strip. To this end, it is possible to use a thickening agent in aqueous phase, as described in the following tests.

For tests n° 53 and n° 54, a slip formulation is produced, the composition and the order of introduction of the constituents of which is given in table 15 (the order of introduction is not fundamental, but by following the chronology the manufacture of the formula is facilitated).

Tests n° 53 (invention) and n° 54 (reference) use respectively a copolymer consisting of:

a) 36.5% of methacrylic acid, b) 44.1% of ethyl acrylate, c) 10.0% of acrylamide, d) 9.4% of the monomer of formula (I) designated mono I'.

and no thickening agent.

Once the blend has been produced the viscosity of the formulation is measured using a Brookfield™ viscometer, at a speed of 10 revolutions/minute.

The slip compositions and the said Brookfield™ viscosities are indicated in table 15.

TABLE 15 composition (by weight of the constituents) of the slips for test n° 53 (invention) and n° 54 (reference) and Brookfield ™ viscosities obtained

| Constituents | Test n° 53 (invention) | Test n° 54 (reference) |
|---|---|---|
| Ordinary water | 204.2 g | 204.2 g |
| Acrylic dispersing agent Coatex ™ GX CE (COATEX ™) | 3.57 g | 3.57 g |
| Blend of ground clays | 500 g | |
| Dispersion whilst stirring for 30 minutes | | |
| Thickening agent | 0.71 g | 0 g |
| Stirring followed by adjustment of pH to a value of 8.5 average of sodium hydroxide 50% | | |
| Brookfield ™ viscosity 10 RPM | 3,600 mPa · s | 900 mPa · s |

Use of the copolymer according to the invention enables the slip to be thickened notably.

EXAMPLE 12

This example illustrates the use of copolymers according to the invention in the leather field.

Skin (leather) items must often be covered with a protective film in order to ensure a uniform appearance and/or water resistance. This protection may be accomplished by the application of a varnish in aqueous phase. The formulation below exemplifies use of the polymer according to the invention in order to thicken an acrylic emulsion based formulation in an aqueous phase, a thickening which is necessary for easy application by every means known to the skilled man in the art. This unthickened formulation has a very low viscosity, leading to dripping when the varnish is applied, if it is not thickened.

For tests n° 55 and n° 56, a varnish formulation is produced, intended for leathers, the composition and the order of introduction of the constituents of which is given in table 16 (the order of introduction is not fundamental, but by following the chronology the manufacture of the formula is facilitated).

Tests n° 55 (prior art) and n° 56 (invention) use respectively a thickening agent according to the prior art, which is a methacrylic/ethyl acrylate acidic copolymer, and the copolymer used in test n° 42.

Once the formulation has been produced, the Brookfield™ viscosity is measured, at 10 and 100 revolutions/minute, in order to check the thickening effect of the products.

The compositions of the formulations and the corresponding Brookfield™ viscosities are indicated in table 16.

TABLE 16 composition (by weight of constituents) of the leather varnish formulations for tests n° 55 (prior art) and n° 56 (invention) and Brookfield ™ viscosities obtained

| Constituents | | Test n° 55 (prior art) | Test n° 56 (invention) |
|---|---|---|---|
| Acrylic emulsion in aqueous phase (varnish) Acronal ™ 18D BASF ™ | | 180 g | 180 g |
| Water | | 62 g | 62 g |
| Triethanolamine | | qsp pH 9-9.5 | qsp pH 9-9.5 |
| Thickening agent | | 2 g | 2 g |
| Triethanolamine | | qsp pH 8-8.5 | qsp pH 8-8.5 |
| Brookfield ™ viscosity | 10 tours/minute | 4,100 mPa · s | 5,500 mPa · s |
| | 100 tours/minute | 890 mPa · s | 1,200 mPa · s |

Use of the copolymer according to the invention enables a viscosity higher than the polymer of the prior art to be obtained.

For tests n° 57 and n° 58, a formulation of the fatty emulsion type for leather is produced.

Very many fatty emulsions are used in treating leather and skins in order to give the finished product characteristics, among other things, but not restrictively, of suppleness and water resistance. These emulsions consisting of oils of animal, vegetal or synthetic origin may be transported over large distances or stored for prolonged periods. The problem of their stability is then posed, a problem which may be partially resolved by increasing their active matter content. However, this increase must often be large in order to obtain a stable emulsion, and generally leads to a very high viscosity, making handling of the product difficult. Use of a thickening polymer enables this disadvantage to be remedied, by providing a high viscosity when at rest, but which is rapidly reduced when the emulsion is handled, enabling a product which is stable but easy to handle to be obtained. The tests below highlight the property of the polymer according to the invention in satisfying this function.

For tests n° 57 and n° 58, a fatty emulsion type formulation intended for leathers is produced, the composition and the order of introduction of the constituents of which is given in table 17 (the order of introduction is not fundamental, but by following the chronology the manufacture of the formula is facilitated).

Tests n° 57 (prior art) and n° 58 (invention) use respectively a thickening agent according to the prior art, which is a methacrylic/ethyl acrylate acidic copolymer, and the copolymer used in test n° 47.

Once the formulation has been produced, the Brookfield™ viscosity at 10 and 100 revolutions/minute is measured in order to check the thickening effect of the products.

The composition of the formulations and the ratio of the Brookfield™ viscosities at 10 and 100 revolutions/minute are indicated in table 17.

TABLE 17 composition (by weight of constituents) of the fatty emulsion type formulations for leather for tests n° 57 (prior art) and n° 58 (invention) and Brookfield™ viscosities obtained

| Constituents | | Test n° 57 (prior art) | Test n° 58 (invention) |
|---|---|---|---|
| Vegetal oil emulsion | | 60 g | 60 g |
| Ordinary water | | 60 g | 60 g |
| Thickening agent | | 2.4 g | 2.4 g |
| Ammonia 28% | | qsp pH 7.3 | qsp pH 7.3 |
| Brookfield™ viscosity | 10 T/min | 800 mPa·s | 11,300 mPa·s |
| | 100 T/min | 225 mPa·s | 2,650 mPa·s |
| Ratio of Brookfield™ viscosities at 10 and 100 rev./minute | | 3.55 | 4.26 |

The copolymer according to the invention enables a Brookfield™ viscosity very much higher than that of the polymer of the prior art to be obtained with, in addition, a higher ratio between the Brookfield™ viscosities at 10 and 100 revolutions/minute, leading—for an identical Brookfield™ viscosity measured at 10 rpm—to greater stability when at rest, accompanied by easier handling through a lower Brookfield™ viscosity measured at 100 revolutions/minute.

EXAMPLE 13

This example illustrates the use of copolymers according to the invention in the drilling field.

When boring wells intended for oil prospecting or prospecting of other matter such as water or gas, the skilled man in the art will have to consolidate the walls of the well when the latter are to be exploited, or in the course of boring, if the need for it becomes apparent. To this end, water-based cement dispersions are commonly used, the simplest composition of which is based on water, thickening agents, dispersing agents and cement. Other products may be used, such as mass addition agents (barita, hematite) or other additives such as foaming or filtrate reducing agents. The formulation below is, therefore, in no case restrictive.

For tests n° 59 and n° 60, a cement dispersion formulation is produced for use in drilling wells, the composition and the order of introduction of the constituents of which is given in table 18 (the order of introduction is not fundamental, but by following the chronology the manufacture of the formula is facilitated).

Tests n° 59 (invention) and n° 60 (reference) use respectively a copolymer consisting of:

a) 8.4% of methacrylic acid, b) 82.2% of ethyl acrylate, c) 9.4% of the monomer of formula (I) designated mono I'.

and no thickening agent.

Once the dispersion has been produced, the viscosity is measured using a Ford™ Cup of diameter 4 mm to check the thickening effect of the polymer according to the invention.

The compositions of the formulations and the viscosities are indicated in table 18.

TABLE 18 composition (by weight of constituents) of the formulations of the cement dispersion type for drilling wells for tests n° 59 (invention) and n° 60 (reference) and Ford™ Cup viscosities obtained

| Constituents | Test n° 59 (invention) | Test n° 60 (reference) |
|---|---|---|
| Cement CEM I 42.5 R | 400 g | 400 g |
| Ordinary water | 300 g | 300 g |
| Thickening agent | 1 g | 0 g |
| Ford Cup viscosity, diameter 4 | 14 seconds | 10 seconds |

A low dose of the copolymer according to the invention enables the dispersion to be thickened.

For tests n° 61 to n° 65, bentonitic muds with a fresh water or seawater base are produced.

When boring a well with the aim of seeking oil, gas or water, the skilled man in the art uses a drilling fluid, among other possibilities, the aim of which is to cool the bit and raise the debris. This drilling fluid is very often water-based, using either fresh water or seawater, and contains various mineral fillers the purpose of which is to give it a certain consistency and a certain density. This drilling mud must have highly controlled viscosity characteristics in order to be able to raise the debris easily, while still being able to be pumped. Use of a thickening polymer enables this viscosity to be adjusted finely in order to be able to satisfy the schedule of specifications defined in the drilling location, and depending on the type of rocky formation traversed. The drilling muds below are produced by mixing with high-speed stirring in a Hamilton Beach™ mixer of the following compounds. The order of introduction is not fundamental, but by following the chronology and the adding times, manufacture of the formula is facilitated.

Synthetic seawater is produced by dissolution in a final volume of 1 litre of the following salts:

| | |
|---|---|
| Sodium chloride | 44.05 g. |
| Potassium chloride | 0.67 g. |
| Dihydrated calcium chloride | 1.36 g. |
| Hexahydrated magnesium chloride | 4.66 g. |
| Heptahydrated magnesium sulphate | 6.29 g. |
| Sodium acid carbonate | 0.18 g. |

After preparation of the drilling fluids, their rheological characteristics are measured using a Fann™ rheometer. Use of the thickening polymer is intended to increase the value of the measured viscosities.

Tests n° 61 (reference), 62 (prior art) and 63 (invention) are relative to fresh water formulations, and use respectively: no thickening agent, a polymer of the prior art which is a methacrylic/ethical acrylate acidic copolymer, and a copolymer consisting of:

a) 35.3% of methacrylic acid, b) 52.7% of ethyl acrylate, c) 12.0% of the monomer of formula (I) designated mono I" consisting of:

Tests n° 64 (reference), 65 (invention) are relative to seawater formulations, and use respectively: no thickening agent, and a copolymer consisting of:

a) 20.8% of methacrylic acid, b) 70.0% of ethyl acrylate, c) 9.2% of the monomer of formula (I) designated mono I".

The compositions and corresponding viscosities are indicated in table 19.

TABLE 19 composition of formulations of fresh water and seawater bentonitic muds, and corresponding Fann™ viscosities

| Constituents | | Test n° 61 (reference) | Test n° 62 (prior art) | Test n° 63 (invention) | Test n° 64 (reference) | Test n° 65 (invention) |
|---|---|---|---|---|---|---|
| Ordinary water | | 375.5 g | 375.5 g | 375.5 g | 0 g | 0 g |
| Synthetic seawater | | 0 g | 0 g | 0 g | 334.8 g | 334.8 g |
| Bentonitic clay Zeogel™ (BAROID™) | | 7.66 g | 7.66 g | 7.66 g | 9 g | 9 g |
| | | \multicolumn{5}{c}{Stirring for 10 minutes} | | | | |
| Bentonitic clay Aquagel™ (BAROID™) | | 6.13 g | 6.13 g | 6.13 g | 7.24 g | 7.24 g |
| | | Stirring for 10 minutes | | | | |
| Barium sulphate (Barita) | | 207 g | 207 g | 207 g | 244 g | 244 g |
| | | Stirring for 15 minutes | | | | |
| Filtrate reducing agent ThermaCheck™ (BAROID™) | | 3.83 g | 3.83 g | 3.83 g | 4.52 g | 4.52 g |
| | | Stirring for 10 minutes followed by adjustment of the pH to 10.5 with sodium hydroxide 50% | | | | |
| Thickening agent | | 0 g | 2.4 g | 2.4 g | 0 g | 0.6 g |
| | | Stirring for 10 minutes followed by measurement of viscosities using a Fann™ viscometer | | | | |
| Fann™ viscosity | 600 RPM | 120 | 195 | 205 | 60 | 114 |
| | 300 RPM | 84 | 138 | 147 | 39 | 81 |
| | 200 RPM | 67 | 111 | 120 | 31 | 67 |
| | 100 RPM | 46 | 75 | 84 | 23 | 52 |
| | 6 RPM | 12 | 19 | 25 | 10 | 30 |
| | 3 RPM | 10 | 16 | 22 | 10 | 29 |
| | 0.3 RPM after 10 minutes at rest | 24 | 58 | 71 | 21 | 47 |

The copolymer according to the invention enables a viscosity higher than the polymer of the prior art to be obtained. This is particularly visible in relation to the measurement at 0.3 RPM made after 10 minutes' rest, which represents the capacity of the mud to keep the debris in suspension when the drilling mud circulation pumps stop. A high value of this measurement is necessary to prevent all sedimentation of the debris at the bottom of the well, which sedimentation would cause the drilling to be stopped.

EXAMPLE 14

This example illustrates the use of copolymers according to the invention in the field of hydraulic binders.

When using hydraulic binders such as cement, the skilled man in the art may be induced to manufacture a cement composition the viscosity of which must be increased in order to favour the properties of the blend on application or when removed early from a cast. This application is of course not restrictive, and the polymer according to the invention may be used whenever thickening is required in a cement or hydraulic binder composition, for any application whatever.

For tests n° 66 and n° 67, a mortar formulation is produced, in a mortar mixer, the composition and the order of introduction of the constituents of which is given in table 20 (the order of introduction is not fundamental, but by following the chronology the manufacture of the formula is facilitated).

Tests n° 66 (invention) and n° 67 (reference) use respectively a copolymer consisting of:

a) 20.0% of methacrylic acid, b) 70.6% of ethyl acrylate, c) 9.4% of the monomer of formula (I) designated mono I'.

and no thickening agent.

Once the formula has been manufactured the viscosity is measured by means of an impact table in order to check the thickening effect of the polymer according to the invention. This thickening leads to a reduced spreading of the mortar cake on the impact table.

The composition of the formulations and the viscosity values obtained are indicated in table 20.

TABLE 20 composition of the mortars, and corresponding spreadings

| Constituents | Test n° 66 (invention) | Test n° 67 (reference) |
|---|---|---|
| Ordinary water | 300 g | 300 g |
| Thickening agent | 3 g | 0 g |
| Lithium hydroxide | 1 g | 1 g |
| Cement CEM I 42.5 R | 450 g | 450 g |
| | Stirring at low speed for 30 seconds | |
| Standardised sand (EN 196-1) Added in 30 seconds | 1,590 g | 1,590 g |
| | Stirring at high speed for 30 seconds Rest for 90 seconds Stirring at high speed for 60 seconds | |
| Spreading on the impact table | 19.6 cm | 24 cm |

The copolymer according to the invention enables the spreading of the mortar to be reduced significantly, revealing an increase of viscosity.

EXAMPLE 15

This example illustrates the use of copolymers according to the invention in the field of plasters.

Plaster of Paris (calcium sulphate, hemi-hydrate) is very often used in binding, gluing or jointing compositions for construction. It may be associated with other fillers, whether mineral or other. Some uses require that the dispersion has a certain viscosity to facilitate its use by the skilled man in the art.

The following formulation is comprised of plaster of Paris and calcium carbonate. Its viscosity is controlled by means of a Schmidt™ ring of internal diameter 6 cm. This ring is placed on a glass plate, filled with the formulation and raised with a rapid and regular movement. The plaster dispersion then spreads as a cake of a diameter proportional to its viscosity. In this case, zero spreading is sought, and the dispersion, although easy to handle, must remain immobile. This formulation, used for example in joints, will remain in place without becoming deformed after its application.

For tests n° 68 and n° 69, a plaster formulation is produced, the composition and the order of introduction of the constituents of which is given in table 21 (the order of introduction is not fundamental, but by following the chronology the manufacture of the formula is facilitated).

Tests n° 68 (prior art) and n° 69 (invention) use respectively a thickening agent according to the prior art, which is an acrylic acid and ethyl acrylate copolymer, and a copolymer consisting of:

a) 36.5% of methacrylic acid, b) 44.1% of ethyl acrylate, c) 10.0% of methacrylamide, d) 9.4% of the monomer of formula (I) designated mono I'.

TABLE 21 composition of the plasters, and corresponding spreadings

| Constituents | Test n° 68 (prior art) | Test n° 69 (invention) |
|---|---|---|
| Calcium sulphate, hemi-hydrate Plaster of Paris | 140 g | 140 g |
| Calcium carbonate Omyacarb ™ 30 AV (OMYA ™) | 40 g | 40 g |
| Ordinary water | 120 g | 120 g |
| Thickening agent | 0.2 g | 0.2 g |
| 2-amino 2-methyl 1-propanol AMP 95 (ANGUS ™) | 0.2 g | 0.2 g |
| Spreading with Schmidt ™ ring | 8 cm | 6 cm |

The copolymer according to the invention enables the formulation to be maintained in place whereas the polymer of the prior art allows a deformation to occur.

EXAMPLE 16

This example concerns the use of polymers according to the invention in the field of paints.

For tests n° 70 to n° 84, paint formulations are produced, from a satin base, and through the addition of a polymer according to the prior art, or by addition of a polymer according to the invention.

The composition of the satin base is as follows (weight in grams):

| | |
|---|---|
| Prolylene glycol: | 40 |
| Water: | 134 |
| Coatex ™ BR3 (COATEX ™): | 5 |
| Mergal ™ K6N (RIEDEL DE HAEN ™): | 2 |
| Nopco ™ NDW (HENKEL ™): | 1 |
| TiO2 RHD2: | 200 |
| Hydrocarb ™ (OMYA ™): | 150 |
| Acronal ™ 290 D (BASF ™): | 420 |
| Butyldiglycol: | 30 |
| Ammonia (31%): | 3 |

Test n° 70 illustrates the prior art and uses 985 grams of the said satin base, together with 14.1 grams of a polymer of the prior art which is a copolymer of methacrylic acid and ethyl acrylate, and 0.9 grams of water.

Tests n° 71 to n° 84 illustrate the invention and use 985 grams of the said satin base, and 15 grams of different copolymers, according to the invention, identified by the number of the tests in which they have already been used.

2 types of tests are then made on these different paint formulations:

A pigmentary compatibility test, which consists in measuring the Brookfield™ viscosity at 10 and 100 revolutions/minute on each formulation, and then after adding 5% by weight relative to the total weight of the formulation of a black pigment which is Colanyl N130 (CLARIANT™); the change in viscosity is then calculated, expressed as a percentage of change relative to the initial viscosity, and noted $\Delta_{10}^{comp}$ and $\Delta_{100}^{comp}$ depending on whether it refers to a measurement made at 10 or 100 revolutions/minute; the lower this variation, the more the pigmentary compatibility proves satisfactory;

a stability test in the kiln, which consists in measuring the Brookfield™ viscosity at 10 and 100 revolutions/minute on each formulation, and then after a stay of 10 days in a kiln at 50° C.; the variation of viscosity is then calculated, expressed as a percentage of change relative to the initial viscosity, and noted $\Delta_{10}^{stab}$ and $\Delta_{100}^{stab}$ depending on whether it refers to a measurement made at 10 or 100 revolutions/minute; the closer this variation is to zero, the better the stability proves;

For tests n° 70 to n° 84, the polymers used, together with the values of $\Delta_{10}^{comp}$ and $\Delta_{100}^{comp}$ obtained for the pigmentary compatibility tests, and the values $\Delta_{10}^{stab}$ and $\Delta_{100}^{stab}$ obtained for the temperature stability tests, are indicated in table 22.

TABLE 22 polymers used in tests n° 70 (prior art) and n° 71 to 84 (invention - the polymers are here identified by the numbers of the tests in which they have been previously used), together with the values of $\Delta_{10}^{comp}$ and $\Delta_{100}^{comp}$ (as a % of relative increase) obtained for the pigmentary compatibility tests, and values of $\Delta_{10}^{stab}$ and $\Delta_{100}^{stab}$ (as a % of relative increase) obtained for the temperature stability tests.

| | Test n° | | | | | | | | | | | | | | |
|---|---|---|---|---|---|---|---|---|---|---|---|---|---|---|---|
| | 70 | 71 | 72 | 73 | 74 | 75 | 76 | 77 | 78 | 79 | 80 | 81 | 82 | 83 | 84 |
| Polymer of test n° | * | 42 | 44 | 49 | 40 | 52 | 53 | 59 | 69 | 66 | 47 | 46 | 65 | 38 | 63 |
| $\Delta_{10}^{comp}$ | 41 | 27 | 40 | 16 | 29 | 15 | 33 | 40 | 21 | 28 | 30 | 22 | 9 | 8 | 5 |
| $\Delta_{100}^{comp}$ | 41 | 27 | 33 | 13 | 26 | 18 | 39 | 26 | 21 | 22 | 30 | 26 | 7 | 14 | 18 |
| $\Delta_{10}^{stab}$ | −35 | −32 | 17 | −9 | −30 | −17 | −10 | −30 | −7 | −25 | −32 | −12 | −19 | −6 | 0 |
| $-\Delta_{100}^{stab}$ | −36 | −23 | 12 | 2 | −28 | −7 | −5 | −32 | −2 | −18 | −29 | 2 | −13 | 4 | 29 |

* copolymer of methacrylic acid and of ethyl acrylate

The results obtained demonstrate that the use of the copolymers according to the invention leads to a pigmentary compatibility, and also a temperature stability, which are systematically improved compared to the polymer of the prior art.

The invention claimed is:

1. An optionally pigmented aqueous formulation comprising a copolymer comprising
a) at least one monomer with ethylenic unsaturation and a carboxylic function,
b) at least one non-ionic monomer with ethylenic unsaturation,
c) at least one oxyalkylated monomer with ethylenic unsaturation terminated by a hydrophobic, non-aromatic branched chain with 12 to 24 carbon atoms, and
d) optionally at least one monomer with at least two ethylenic unsaturations,
wherein the hydrophobic, non-aromatic branched chain with 12 to 24 carbon atoms has two branches each having at least 6 carbon atoms.

2. The formulation according to claim 1, wherein
a) the monomer or monomers with ethylenic unsaturation and a carboxylic function are selected from the group consisting of acrylic acid, methacrylic acid, $C_1$ to $C_4$ monoesters of maleic or itaconic acids, and mixtures thereof, or are selected from the group of monomers with ethylenic unsaturation and a dicarboxylic function, consisting of crotonic, isocrotonic, cinnamic, itaconic, maleic acid, and maleic anhydride,
b) the non-ionic monomer or monomers with ethylenic unsaturation are selected from the group consisting of the methyl, ethyl, butyl or 2-ethyl-hexyl esters of acrylic and methacrylic acid, among acrylonitrile, vinyl acetate, styrene, methylstyrene, diisobutylene, vinylpyrrolidone, and vinylcaprolactam,
c) the oxyalkylated monomer or monomers with ethylenic unsaturation and terminated by a hydrophobic and non-aromatic branched chain with 12 to 24 carbon atoms, have the following formula:

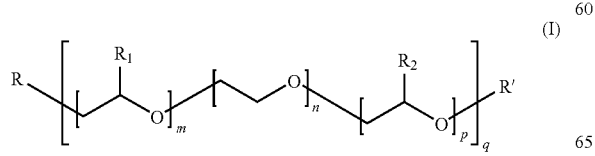

(I)

wherein:

m and p represent a number of alkylene oxide units of between 0 and 150, n represents a number of ethylene oxide units of between 5 and 150, q represents a whole number at least equal to 1 and such that $15 \leq (m+n+p) \leq 120$, $R_1$ represents the methyl or ethyl radical, $R_2$ represents the methyl or ethyl radical, R represents a radical containing a polymerisable unsaturated function belonging to the group of acrylic, methacrylic, maleic, itaconic or crotonic esters, and R' represents a hydrophobic and non-aromatic branched chain with 12 to 24 carbon atoms with two branches each having at least 6 carbon atoms, and d) the optional monomer or monomers, called crosslinking monomers, with at least two ethylenic unsaturations, are selected from the group consisting of ethylene glycol diacrylate, ethylene glycol dimethacrylate, trimethylolpropanetriacrylate, trimethylolpropanetrimethacrylate, allyl acrylate, methylenebisacrylamide, methylenebismethacrylamide, tetrallyloxyethane, triallylcyanurates, and allylic ethers of pentaerythritol, sorbitol, or sucrose.

3. The formulation according to claim 1, wherein the copolymer contains, expressed by weight:
a) 2 to 95% of at least one monomer with ethylenic unsaturation and a carboxylic function selected from the group consisting of acrylic acid, methacrylic acid, $C_1$ to $C_4$ monoesters of maleic or itaconic acids, and mixtures thereof, or are selected from the group of monomers with ethylenic unsaturation and a dicarboxylic function, consisting of crotonic, isocrotonic, cinnamic, itaconic, maleic acid, and maleic anhydride,
b) 2 to 95% of at least one non-ionic monomer with ethylenic unsaturation selected from the group consisting of the methyl, ethyl, butyl or 2-ethyl-hexyl esters of acrylic and methacrylic acid, acrylonitrile, vinyl acetate, styrene, methylstyrene, diisobutylene, vinylpyrrolidone, and vinylcaprolactam,
c) 2 to 25% of at least one monomer with ethylenic unsaturation and terminated by a hydrophobic and non-aromatic branched chain with 12 to 24 carbon atoms, having the following formula:

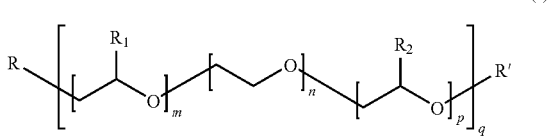

wherein:

m and p represent a number of alkylene oxide units of between 0 and 150, n represents a number of ethylene oxide units of between 5 and 150, q represents a whole number at least equal to 1 and such that $15 \leqq (m+n+p) \leqq 120$ $R_1$ represents the methyl or ethyl radical, $R_2$ represents the methyl or ethyl radical, R represents a radical containing a polymerisable unsaturated function belonging to the group of acrylic, methacrylic, maleic, itaconic or crotonic esters, and R' represents a hydrophobic and non-aromatic branched chain with 12 to 24 carbon atoms with two branches each having at least 6 carbon atoms, and d) 0% to 3% of at least one monomer with at least two ethylenic unsaturations selected from the group consisting of ethylene glycol diacrylate, ethylene glycol dimethacrylate, trimethylolpropanetriacrylate, trimethylolpropanetrimethacrylate, allyl acrylate, methylenebisacrylamide, methylenebismethacrylamide, tetrallyloxyethane, triallylcyanurates, and allylic ethers of pentaerythritol, sorbitol, or sucrose, where the total by weight of the monomers a), b), c) and d) is equal to 100%.

4. The formulation according to claim 3 wherein the hydrophobic branched and non-aromatic chain of monomer c) has 16 to 20 carbon atoms, and has 2 branchings with least 6 carbon atoms.

5. The formulation according to claim 4 wherein the hydrophobic branched and non-aromatic chain of monomer c) is 2 hexyl 1-decanyl or 2-octyl 1-dodecanyl.

6. The formulation according to claim 1, wherein the copolymer does not contain the crosslinking monomer d).

7. The formulation according to claim 1 wherein the copolymer is in acid form, or partially or totally neutralised by one or more neutralisation agents having a monovalent neutralising function selected from the group consisting of sodium, potassium, lithium, ammonium, aliphatic stearylamine, ethanolamines (mono-, di- or tri-ethanolamine), mono- di-ethylamine, cyclohexylamine, methylcyclohexylamine, 2-amino 2-methyl 1-propanol and morpholine.

8. The formulation according to claim 1, wherein the formulation is in the form of dispersion paints, varnishes, paper coatings, cosmetics, detergence, textile formulations and drilling muds.

9. A thickening agent enabling the viscosity of the aqueous formulations to be developed and/or maintained in the presence of compounds, or when the said compounds are added to the said formulations, the thickening agent is comprising a water-soluble acrylic copolymer comprising:

a) at least one monomer with ethylenic unsaturation and a carboxylic function, b) at least one non-ionic monomer with ethylenic unsaturation, c) at least one oxyalkylated monomer with ethylenic unsaturation terminated by a hydrophobic, non-aromatic branched chain with 12 to 24 carbon atoms, and d) optionally at least one monomer with at least two ethylenic unsaturations, wherein the hydrophobic, non-aromatic branched chain with 12 to 24 carbon atoms has two branches each having at least 6 carbon atoms.

10. A thickening agent according to claim 9, wherein a) the monomer or monomers with ethylenic unsaturation and a carboxylic function are selected from the group consisting of acrylic acid, methacrylic acid, $C_1$ to $C_4$ monoesters of maleic or itaconic acids, and mixtures thereof, or are selected from the of monomers with ethylenic unsaturation and a dicarboxylic function, consisting of crotonic, isocrotonic, cinnamic, itaconic, maleic acid, and maleic anhydride, b) the non-ionic monomer or monomers with ethylenic unsaturation are selected from the group consisting of the methyl, ethyl, butyl or 2-ethyl-hexyl esters of acrylic and methacrylic acid, acrylonitrile, vinyl acetate, styrene, methylstyrene, diisobutylene, vinylpyrrolidone, and vinylcaprolactam, c) the oxyalkylated monomer or monomers with ethylenic unsaturation and terminated by a hydrophobic and non-aromatic branched chain with 12 to 24 carbon atoms, have the following formula:

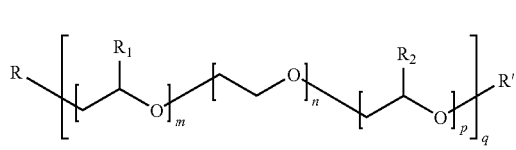

wherein:

m and p represent a number of alkylene oxide units of between 0 and 150, n represents a number of ethylene oxide units of between 5 and 150, q represents a whole number at least equal to 1 and such that $15 \leqq (m+n+p) \leqq 120$ $R_1$ represents the methyl or ethyl radical, $R_2$ represents the methyl or ethyl radical, R represents a radical containing a polymerisable unsaturated function belonging to the group of acrylic, methacrylic, maleic, itaconic or crotonic esters, and R' represents a hydrophobic and non-aromatic branched chain with 12 to 24 carbon atoms with two branches each having at least 6 carbon atoms, and d) the optional monomer or monomers, called crosslinking monomers, with at least two ethylenic unsaturations, are selected from the group consisting of ethylene glycol diacrylate, ethylene glycol dimethacrylate, trimethylolpropanetriacrylate, trimethylolpropanetrimethacrylate, allyl acrylate, methylenebisacrylamide, methylenebismethacrylamide, tetrallyloxyethane, triallylcyanurates, and allylic ethers of pentaerythritol, sorbitol, or sucrose.

11. A thickening agent according to claim 10, wherein the copolymer comprises, expressed by weight:

a) 2 to 95% of at least one monomer with ethylenic unsaturation and a carboxylic function selected from the group consisting of acrylic acid, methacrylic acid, $C_1$ to $C_4$ monoesters of maleic or itaconic acids, and mixtures thereof, or are selected from the group of monomers with ethylenic unsaturation and a dicarboxylic function, consisting of crotonic, isocrotonic, cinnamic, itaconic, maleic acid, and maleic anhydride, b) 2 to 95% of at least one non-ionic monomer with ethylenic unsaturation selected from the group consisting of the methyl, ethyl, butyl or 2-ethyl-hexyl esters of acrylic and methacrylic acid, acrylonitrile, vinyl acetate, styrene, methylstyrene, diisobutylene, vinylpyrrolidone, and vinylcaprolactam, c) 2 to 25% of at least one monomer with ethylenic unsaturation and terminated by a hydrophobic and non-aromatic branched chain with 12 to 24 carbon atoms, having the following formula:

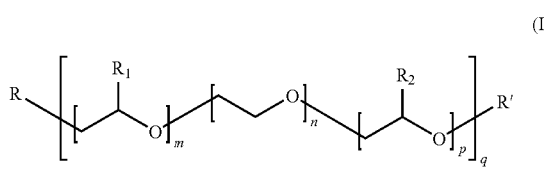

(I)

wherein:

m and p represent a number of alkylene oxide units of between 0 and 150, n represents a number of ethylene oxide units of between 5 and 150, q represents a whole number at least equal to 1 and such that $15 \leq (m+n+p) \leq 120$, $R_1$ represents the methyl or ethyl radical, $R_2$ represents the methyl or ethyl radical, R represents a radical containing a polymerisable unsaturated function belonging to the group of acrylic, methacrylic, maleic, itaconic or crotonic esters, and R' represents a hydrophobic and non-aromatic branched chain with 12 to 24 carbon atoms with two branches each having at least 6 carbon atoms, and d) 0% to 3% of at least one monomer with at least two ethylenic unsaturations selected from the group consisting of ethylene glycol diacrylate, ethylene glycol dimethacrylate, trimethylolpropanetriacrylate, trimethylolpropanetrimethacrylate, ally acrylate, methylenebisacrylamide, methylenebismethacrylamide, tetrallyloxyethane, triallylcyanurates, and allylic ethers of pentaerythritol, sorbitol, or sucrose, where the total by weight of the monomers a), b), c) and d) is equal to 100%.

12. The thickening agent according to claim 11 wherein the hydrophobic branched and non-aromatic chain of monomer c) has 16 to 20 carbon atoms, and has 2 branchings with least 6 carbon atoms.

13. The thickening agent according to claim 12, wherein the hydrophobic branched and non-aromatic chain of monomer c) is 2-hexyl 1-decanyl or 2-octyl 1-dodecanyl.

14. The thickening agent according to claim 9, wherein the thickening agent does not contain the crosslinking monomer d).

15. The thickening agent according to claim 9, wherein the copolymer is in acid form, or partially or totally neutralised by one or more neutralisation agents having a monovalent neutralising function selected from the group consisting of sodium, potassium, lithium, ammonium, aliphatic stearylamine, ethanolamines (mono-, di- or tri-ethanolamine), mono- di-ethylamine, cyclohexylamine, methylcyclohexylamine, 2-amino 2-methyl 1-propanol and morpholine.

16. A process to manufacture optionally pigmented aqueous formulations, comprising adding the thickening agent according to claim 9 to the formulations in the presence of salts or surfactants, or when the said salts or surfactants are added to the aqueous formulations.

17. An optionally pigmented aqueous formulation comprising the thickening agent according to claim 9.

18. The aqueous coating formulation according to claim 17, wherein the formulation is selected from the group consisting of dispersion paints, varnishes, paper coatings, cosmetic formulations, detergent formulations, textile formulations and drilling muds.

19. The aqueous formulation according to claim 17, wherein the formulation is selected from the group consisting of formulations of joint filler for plasterboard, formulations for ceramics, formulations for leather, plaster formulations, formulations for hydraulic binders and mortar formulations.

* * * * *

UNITED STATES PATENT AND TRADEMARK OFFICE
CERTIFICATE OF CORRECTION

PATENT NO.        : 7,790,800 B2
APPLICATION NO.   : 11/631474
DATED             : September 7, 2010
INVENTOR(S)       : Jean-Marc Suau et al.

It is certified that error appears in the above-identified patent and that said Letters Patent is hereby corrected as shown below:

Column 8, line 30, "highlight the pigmentary compatibility Theological proper-", should read --highlight the pigmentary compatibility rheological proper- --

Column 20, line 65, Table 9, "Texapoan NSO", should read --Texapon NSO--

Column 24, line 27, "d) 9.4% of the monomer of formula (J) designated mono I'.", should read --d) 9.4% of the monomer of formula (I) designated mono I'.--

Column 24, line 37, Table 14, "cpmposition (by weight of constituents) for tests n° 51 (prior art) and", should read --composition (by weight of constituents) for tests n° 51 (prior art) and--

Column 33, line 52, Claim 1 "and methacrylic acid, among acrylonitrile, vinyl acetate," should read --and methacrylic acid, acrylonitrile, vinyl acetate--

Column 35, line 62, Claim 9, "the said formulations, the thickening agent is comprising a" should read --the said formulations, the thickening agent comprising a--

Column 36, line 14, Claim 10, "thereof, or are selected from the of monomers with eth-", should read --thereof, or are selected from the monomers with eth- --

Column 37, line 42, Claim 11, "ethylolpropanetrimethacrylate, ally acrylate, methyl-" should read --ethylolpropanetrimethacrylate, allyl acrylate, methyl- --

Signed and Sealed this
Twenty-fifth Day of January, 2011

David J. Kappos
*Director of the United States Patent and Trademark Office*